US010416086B2

(12) United States Patent
Kido

(10) Patent No.: US 10,416,086 B2
(45) Date of Patent: Sep. 17, 2019

(54) IMAGE INSPECTION DEVICE

(71) Applicant: Keyence Corporation, Osaka (JP)

(72) Inventor: Manabu Kido, Osaka (JP)

(73) Assignee: Keyence Corporation, Osaka (JP)

( * ) Notice: Subject to any disclaimer, the term of this patent is extended or adjusted under 35 U.S.C. 154(b) by 0 days.

(21) Appl. No.: 15/925,803

(22) Filed: Mar. 20, 2018

(65) Prior Publication Data
US 2018/0328855 A1 Nov. 15, 2018

(30) Foreign Application Priority Data
May 9, 2017 (JP) .................. 2017-093359

(51) Int. Cl.
*G01N 21/00* (2006.01)
*G01N 21/88* (2006.01)
(Continued)

(52) U.S. Cl.
CPC ..... *G01N 21/8806* (2013.01); *G01B 11/2509* (2013.01); *G01B 11/2513* (2013.01);
(Continued)

(58) Field of Classification Search
CPC .......... G01N 21/8851; G01N 21/8806; G01N 21/896; G01N 21/88; G01N 2021/8845;
(Continued)

(56) References Cited

U.S. PATENT DOCUMENTS 7,394,084 B2 * 7/2008 Kuriyama .......... G01N 21/8806
250/559.34
8,077,307 B2 * 12/2011 Pertzov .............. G01N 21/8806
356/237.1
(Continued)

FOREIGN PATENT DOCUMENTS

JP H09-126890 5/1997
JP 2007-206797 8/2007

OTHER PUBLICATIONS

U.S. Appl. No. 15/925,805, filed Mar. 20, 2018 (97 pages).
(Continued)

*Primary Examiner* — Hoa Q Pham
(74) *Attorney, Agent, or Firm* — Kilyk & Bowersox, P.L.L.C.

(57) ABSTRACT

The invention alleviates a burden on a user relating to an image inspection device based on photometric stereo and multi-spectral imaging. An illumination device 3 has three or more illumination blocks that irradiate a workpiece 2 with illumination beams from different directions, respectively. A camera 4 generates images of the workpiece 2. An image processing device 5 irradiates the workpieces 2 sequentially with illumination beams from light emitting elements of different lighting colors and generates a plurality of spectral images. The image processing device 5 sequentially turns on the three or more illumination blocks in units of blocks and generates a plurality of direction images. The image processing device 5 generates a color inspection image based on the plurality of spectral images and executes color inspection. The image processing device 5 generates a shape inspection image based on the plurality of direction images and executes shape inspection.

18 Claims, 25 Drawing Sheets

(51) Int. Cl.
*G01N 21/27* (2006.01)
*G01B 11/30* (2006.01)
*G01B 11/25* (2006.01)
*G06T 7/00* (2017.01)

(52) U.S. Cl.
CPC ........ *G01B 11/2545* (2013.01); *G01B 11/303* (2013.01); *G01N 21/27* (2013.01); *G01N 21/8851* (2013.01); *G06T 7/0004* (2013.01); *G01N 2021/8845* (2013.01); *G01N 2021/8887* (2013.01); *G01N 2201/061* (2013.01)

(58) Field of Classification Search
CPC ............ G01N 2201/0626; G01B 11/24; G01B 9/02087
USPC .................. 356/601–623, 237.1–237.5, 394; 382/103, 141, 145, 152; 250/208.1, 250/578.1; 348/131
See application file for complete search history.

(56) References Cited

U.S. PATENT DOCUMENTS

| | | | |
|---|---|---|---|
| 8,615,125 B2* | 12/2013 | Mori | G06T 7/0004 356/237.2 |
| 9,494,528 B2* | 11/2016 | Matsuda | G01N 21/8806 |
| 10,168,216 B2* | 1/2019 | Kido | G01J 3/462 |
| 10,304,176 B2* | 5/2019 | Kido | G06T 7/0004 |
| 2004/0061850 A1* | 4/2004 | Fisch | G01N 21/8806 356/237.2 |
| 2004/0184031 A1* | 9/2004 | Vook | G06T 7/0002 356/237.1 |
| 2005/0146716 A1* | 7/2005 | Dixon | G01N 21/278 356/237.4 |
| 2005/0190361 A1* | 9/2005 | Ishiba | G01N 21/95684 356/237.2 |
| 2009/0135434 A1* | 5/2009 | Keranen | B41F 33/0036 356/611 |
| 2010/0289893 A1* | 11/2010 | Yoo | G01B 11/24 348/135 |
| 2015/0022637 A1* | 1/2015 | Saeki | G06T 7/0004 348/46 |
| 2018/0328789 A1* | 11/2018 | Kido | G01J 3/462 |
| 2018/0330489 A1* | 11/2018 | Kido | G06T 7/0004 |
| 2018/0330490 A1* | 11/2018 | Kido | G06T 7/0004 |

OTHER PUBLICATIONS

U.S. Appl. No. 15/925,804, filed Mar. 20, 2018 (75 pages).
U.S. Appl. No. 15/925,802, filed Mar. 20, 2018 (85 pages).
U.S. Appl. No. 15/925,801, filed Mar. 20, 2018 (74 pages).

\* cited by examiner $$\begin{pmatrix} I_1 \\ I_2 \\ I_3 \\ I_4 \end{pmatrix} = \rho L \begin{pmatrix} s_{11} & s_{12} & s_{13} \\ s_{21} & s_{22} & s_{23} \\ s_{31} & s_{32} & s_{33} \\ s_{41} & s_{42} & s_{43} \end{pmatrix} \begin{pmatrix} n_x \\ n_y \\ n_z \end{pmatrix} \quad \cdots \text{EQUATION 1}$$

$$z_{x,y}^{n+1} = \frac{1}{4}\left(z_{x+1,y}^n + z_{x,y+1}^n + z_{x-1,y}^n + z_{x,y-1}^n\right)$$
$$- \frac{w}{8}\left(p_{x+1,y} - p_{x-1,y} + q_{x,y+1} - q_{x,y-1}\right) \quad \cdots \text{EQUATION 2}$$

IMAGE INSPECTION DEVICE

CROSS-REFERENCE TO RELATED APPLICATIONS

The present application claims foreign priority based on Japanese Patent Application No. 2017-093359, filed May 9, 2017, the contents of which is incorporated herein by reference.

BACKGROUND OF THE INVENTION

1. Field of the Invention

The present invention relates to an image inspection device, and particularly to a technique for inspecting an inspection target object using multi-spectral imaging or photometric stereo.

2. Description of Related Art

A workpiece appearance inspection has been widely carried out by capturing an image of a workpiece as an inspection target object to acquire a workpiece image and applying image processing to the workpiece image. A defect of the workpiece appears as unevenness of a reflectance (color) of a surface of the workpiece or appears as unevenness of a shape (irregularities of the surface) thereof.

JP H09-126890 A proposes a color detecting apparatus which captures an image of an inspection target object such as a printed matter to acquire color information and executes color inspection with high accuracy. JP 2007-206797 A proposes measuring an accurate three-dimensional shape of a workpiece (a product to be inspected) using a principle of photometric stereo (PS).

When a color defect and a shape defect exist in one workpiece, both of an image inspection device that inspects the color defect and an image inspection device that inspects the shape defect are required in the related art. In this case, it is necessary to install dedicated illumination and camera for each image inspection device and appropriately set a focus of each camera, which lacks usability. Therefore, an object of the present invention is to alleviate a burden on a user relating to setting of an image inspection device that inspects a color defect and a shape defect.

SUMMARY OF THE INVENTION

An image inspection device according to a first embodiment of the present invention includes: an illumination unit which includes three or more illumination blocks that irradiate a target object with illumination beams from mutually different directions, each of the illumination blocks including a plurality of light emitting elements that generate the illumination beams having mutually different wavelengths; an imaging unit which receives light reflected from the target object illuminated by the illumination beams and generates an image of the target object; a control unit which controls the illumination unit to irradiate the target object sequentially with the illumination beams from the light emitting elements of mutually different wavelengths included in the three or more illumination blocks, control the imaging unit to generate a plurality of wavelength images having the mutually different wavelengths of the illuminations beams, controls the illumination unit to irradiate the target object with the illumination beams by sequentially turning on the three or more illumination blocks in units of blocks, and controls the imaging unit to generate a plurality of direction images having mutually different irradiation directions of the illumination beams; an image generation unit which generates a color inspection image in which each pixel has a value corresponding to a color of the target object based on the plurality of wavelength images and generates a shape inspection image which has a value corresponding to irregularities of the target object based on the plurality of direction images; and an inspection unit which executes color inspection of the target object using the color inspection image generated by the image generation unit and executes shape inspection of the target object using the shape inspection image generated by the image generation unit.

According to the present invention, the illumination unit and the imaging unit are used in combination to generate the color inspection image and the shape inspection image, and thus, the burden on the user is alleviated.

DETAILED DESCRIPTION OF PREFERRED EMBODIMENT

One embodiment of the present invention will be described below. Individual embodiments to be described below will be useful for understanding various concepts of the present invention such as superordinate concepts, intermediate concepts, and subordinate concepts. In addition, it should be understood that the technical scope of the present invention is defined by the scope of the claims and is not limited by the individual embodiments below.

Figure 1:
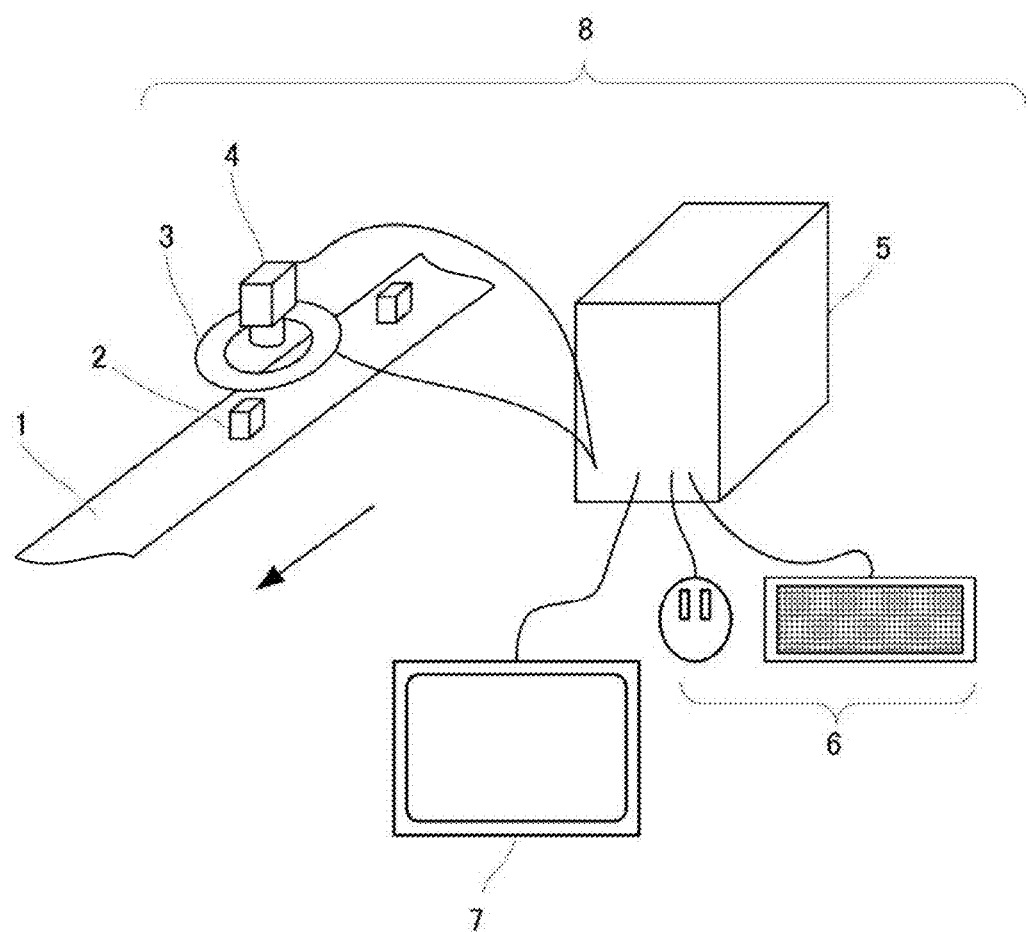
FIG. 1 is a view illustrating an image inspection device.

FIG. 1 is a view illustrating an example of a visual inspection system (image inspection device 8). A line 1 is a conveyor belt or the like for conveying a workpiece 2 which is an inspection target object. An illumination device 3 is an example of an illumination unit which includes a plurality of light emitting elements that generate inspection light (illumination beams) of mutually different wavelengths, and individually irradiates the target object with the illumination beam of each wavelength. A plurality of light emitting elements having the same wavelength may be provided in order to irradiate the workpiece 2 with the illumination beam simultaneously or sequentially from a plurality of directions. A camera 4 is an example of an imaging section for receiving light reflected from the inspection target object illuminated by the illumination beam and generating a luminance image (spectral image). An image processing device 5 includes an inspection unit which illuminates the inspection target object to be subjected to image inspection by sequentially turning on the light emitting elements at illumination intensity set for each wavelength, and executes the image inspection using a plurality of inspection images acquired by the imaging unit. A display unit 7 is a display device which displays a user interface for setting a control parameter relating to the inspection, the inspection images, and the like. An input unit 6 is a console, a pointing device, a keyboard, or the like, and is used to set the control parameter.

<Configuration of Illumination Device>

Figure 2A:
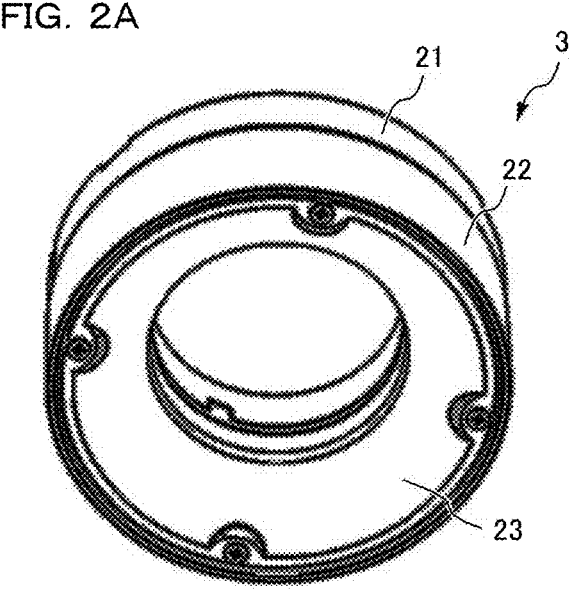
FIGS. 2A to 2D are views illustrating an illumination device.
Figure 2B:
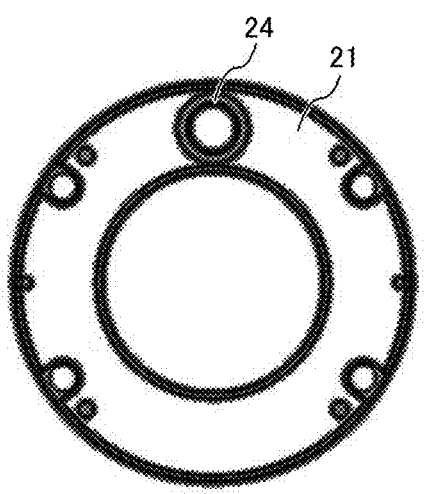
Figure 2C:
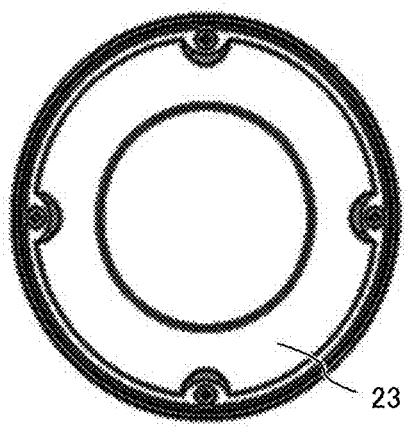
Figure 2D:
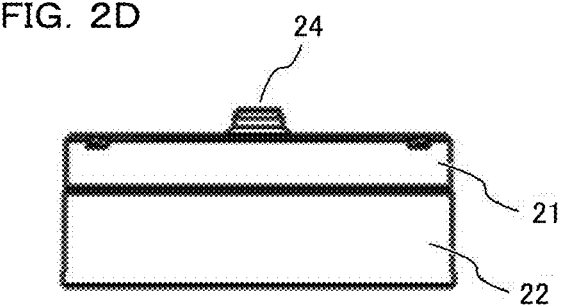

FIG. 2A is a perspective view of the illumination device 3. FIG. 2B is a top view of the illumination device 3. FIG. 2C is a bottom view of the illumination device 3. FIG. 2D is a side view of the illumination device 3. A casing of the illumination device 3 includes an upper case 21 and a lower case 22. A light diffusing member 23 which diffuses light output from each of a plurality of light sources (light emitting elements such as LEDs) is arranged at a lower part of the lower case 22. As illustrated in FIGS. 2A and 2C, the light diffusing member 23 also has an annular shape similarly to the upper case 21 and the lower case 22. As illustrated in FIGS. 2B and 2D, a connector 24 is provided on an upper surface of the upper case 21. A cable for communication between an illumination control board housed in the illumination device 3 and the image processing device 5 is connected to the connector 24. Some functions mounted on the illumination control board may be provided outside the illumination device 3 as an illumination controller. That is, the illumination controller may be interposed between the illumination device 3 and the image processing device 5.

Figure 3A:
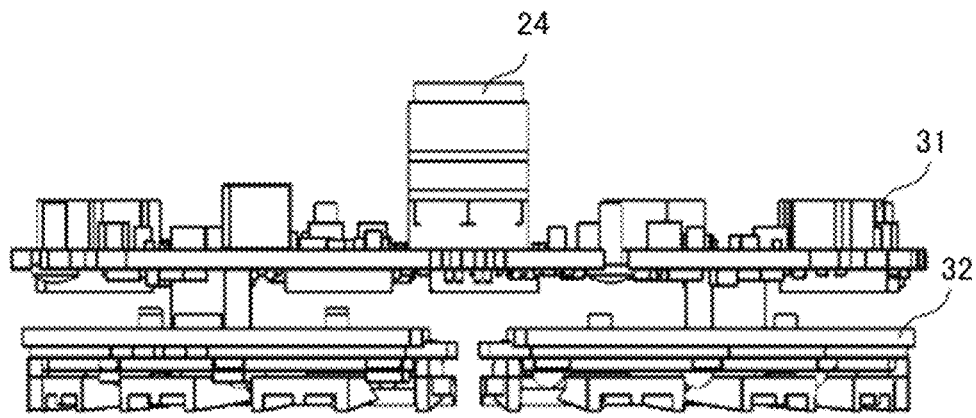
FIGS. 3A to 3E are views illustrating parts constituting the illumination device.
Figure 3B:
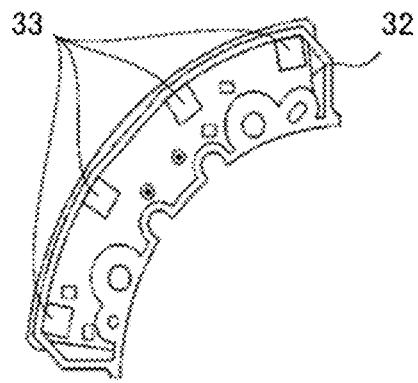
Figure 3C:
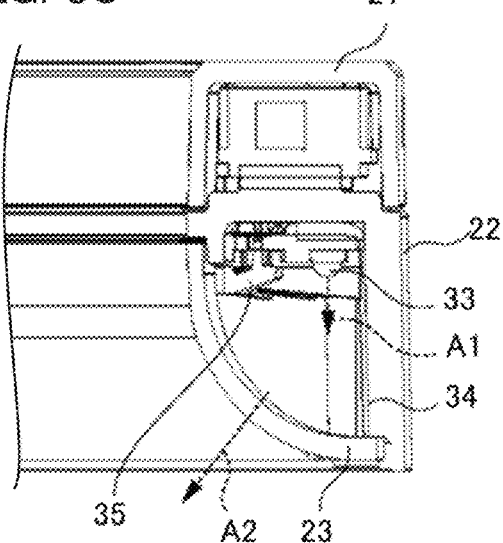
Figure 3D:
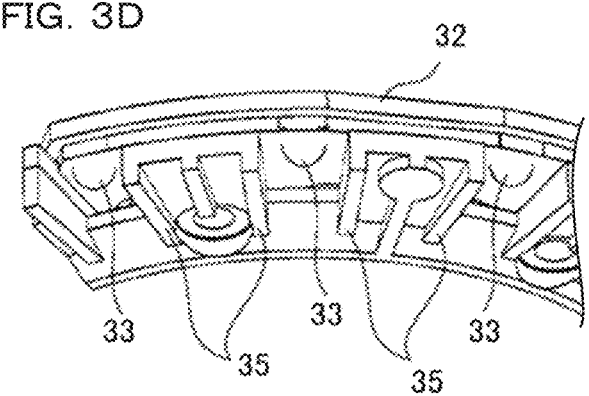
Figure 3E:
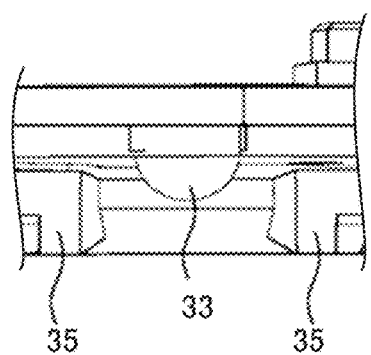

FIG. 3A is a side view illustrating a control board 31 and an LED board 32 housed in the illumination device 3. The control board 31 is an example of a second board on which a lighting control unit is mounted. The LED board 32 is an example of a first board on which the plurality of light sources are mounted. FIG. 3B is a top view of the LED board 32. FIG. 3C is an enlarged cross-sectional view of the vicinity of an LED 33 in the illumination device 3. FIG. 3D is a bottom view of the LED board 32. FIG. 3E is an enlarged side view of the vicinity of the LED 33 in the LED board 32.

The illumination control board and the connector 24 are arranged on the control board 31. The light emitting elements such as LEDs constituting a light source group are mounted on the LED board 32. As illustrated in FIG. 3B, four LED boards 32 are provided for irradiation of the illumination beam from four directions in the present embodiment. That is, one LED board 32 forms one illumination block. As the irradiation of the illumination beam from the four directions is possible, it is possible to acquire a photometric stereo image. That is, the illumination device 3 may be used not only for multi-spectral imaging (MSI) but also for photometric stereo. In a case where four LEDs 33 are arranged on the one LED board 32, the light source group is constituted by sixteen light emitting elements. Meanwhile, a larger number of light emitting elements may be provided. For example, eight LEDs 33 may be arranged on the one LED board 32, and wavelengths of light emitted by the eight LEDs 33 may be different from each other. As illustrated in FIGS. 3C, 3D, and 3E, a light shielding member 35 is arranged between the two adjacent LEDs 33 among the plurality of LEDs 33. When a large number of the LEDs 33 are closely arranged, illumination beams irradiated, respectively, from the two adjacent LEDs 33 may pass through the same region of the light diffusing member 23 in some cases. In this case, the surface of the workpiece 2 is irradiated with the illumination beams with the same amount of light from the same illumination direction in both of a case where one of the LEDs 33 is turned off and the other LED 33 is turned on and a case where the other LED 33 is turned off and the one LED 33 is turned on according to a lighting pattern. Then, it is difficult to generate the inspection images with high accuracy. Thus, a balance between uniformity of the amount of light and independence of the light source is obtained for the two adjacent LEDs 33 by arranging the light shielding member 35 between the two adjacent LEDs 33. As illustrated in FIG. 3C, a light emission direction A1 of the LED 33 does not coincide with a main illumination direction A2. Thus, the light emitted from the LED 33 is deflected toward the light diffusing member 23 by arranging a reflector 34. As a result, it is possible to efficiently irradiate the workpiece 2 with the light emitted from the LED 33. The emission direction A1 and a reflection direction of the reflector 34 are substantially orthogonal to each other in this example since a cross-sectional shape of the light diffusing member 23 forms an arc (FIG. 3C)) and an angle (central angle) of the arc is about 90 degrees. As the central angle is set large in this manner, it is easy to irradiate the surface of the workpiece 2 with substantially uniform parallel light even if the illumination device 3 is moved away from or close to the workpiece 2.

Figure 25:
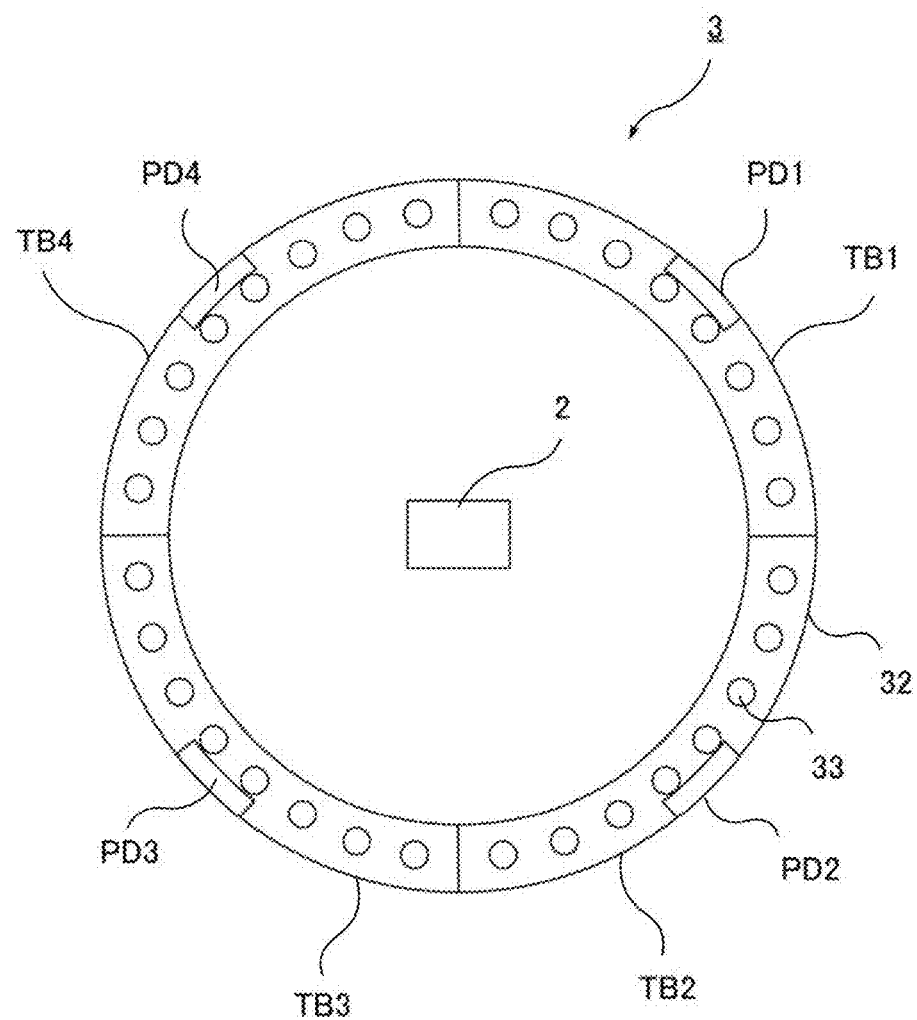
FIG. 25 is a diagram illustrating the illumination device.

FIG. 25 is a schematic plan view of the illumination device 3. The plurality of LEDs 33 that emit light of mutually different wavelengths are arranged in an annular shape on the LED board 32 of the illumination device 3. The illumination control board (FIG. 4) provided on the control board 31 simultaneously turns on the plurality of LEDs 33 having the same wavelength. The plurality of LEDs 33 having the same wavelength are arranged on the LED board 32 at equal intervals. As the plurality of LEDs 33 having each wavelength are simultaneously turned on, the workpiece 2 is irradiated with the substantially uniform illumination beam from an obliquely upper side of the workpiece 2. Accordingly, the camera 4 can capture an omni-directional illumination image of the workpiece 2 corresponding to the respective wavelengths that does not depend on an irradiation direction.

The illumination device 3 is constituted by four illumination blocks TB1 to TB4 each of which includes the plurality of LEDs 33. The plurality of LEDs 33 that emit light of mutually different wavelengths are arranged in each illumination block. Each illumination block includes the LEDs 33 of all wavelength types provided in the illumination device 3. Light receiving elements PD1 to PD4 for light amount feedback control are arranged in each illumination block. The illumination control board controls a current value to be supplied to each of the LEDs 33 such that a light amount of each illumination block is maintained at a light amount set in advance based on a receiving amount of light received by the light receiving elements PD1 to PD4.

The LEDs 33 of the respective wavelengths are arranged in the same number and at equal intervals in the respective illumination blocks. In the example illustrated in FIG. 25, the LEDs 33 of eight wavelengths are arranged one by one at equal intervals in each illumination block. Each illumination block may include two or more LEDs 33 of the same wavelength. In this case, each illumination block is provided with a multiple of the number of wavelengths, for example, 16 (8 wavelengths×2), 24 (8 wavelengths×3), or 32 (8 wavelengths×4) LEDs 33. The plurality of LEDs 33 having the same wavelength are arranged at equal intervals in each illumination block. The above-described arrangement of the LEDs 33 is common to all the illumination blocks. A ring-type illumination is configured by arranging the plurality of illumination blocks in an annular shape. That is, the LEDs 33 having the same wavelength are arranged at equal intervals in the annular shape.

The illumination control board can perform individual lighting control of the illumination device 3 in units of wavelengths. When the LED 33 of a single wavelength, for example, red is turned on, the illumination control board simultaneously turns on the red LEDs 33 included in all the illumination blocks. By sequentially turning on the LEDs 33 of each wavelength, the illumination control board can irradiate the workpiece 2 sequentially with light of different wavelengths. In addition, the illumination control board can perform individual lighting control of each illumination block. For example, the illumination control board may turn on the LEDs 33 included in the illumination block TB1 and turn off the LEDs 33 included in the illumination blocks TB2 to TB4. In addition, the illumination control board can also turn on the illumination blocks TB1 to TB4 sequentially (in the order of TB1, TB2, TB3, TB4). By switching the illumination block to be turned on by the illumination control board, a plurality of luminance images of the workpiece 2 illuminated from different directions may be acquired and used for inspection. Further, the illumination control board can also perform individual lighting control of the LED 33 in units of both wavelengths and illumination blocks. For example, the illumination control board can turn on only the red LED 33 included in the illumination block TB1.

By performing the lighting control of the LEDs 33 in units of wavelengths in this manner, the illumination device 3 irradiates the workpiece 2 with light of different wavelengths. In addition, by performing the lighting control of the LEDs 33 in units of the respective illumination block, it is possible to irradiate the workpiece 2 with light from different irradiation directions.

Not only the monochromatic LED 33 but also the white LED 33 that emits white light in which beams of a plurality of wavelengths are mixed may be arranged on the control board 31. The illumination control board may selectively turn on only the white LED 33 so that the illumination device 3 in the present embodiment is made to function in the same manner as a typical white ring illumination. Further, the illumination control board can also irradiate the workpiece 2 with substantially the white light by simultaneously turning on the LEDs 33 of all wavelengths.

In the present specification, the image obtained by the illumination control board irradiating the workpiece 2 with the illumination beam of the monochromatic wavelength is called a spectral image. In addition, the image obtained by turning on the LEDs 33 of all wavelengths or turning on the white LED 33 is distinguished from the spectral image and is called a white image. The spectral image and the white image may be collectively referred to as the luminance image. Each pixel of the luminance image indicates a luminance value obtained from the camera 4.

Each illumination block is provided with the illumination control board. When each illumination block includes the plurality of LEDs 33 having the same wavelength, the LEDs 33 having the same wavelength are connected in series to each illumination control board, and the LEDs 33 having different wavelengths are connected in parallel.

According to the above drawings, the plurality of LEDs 33 are arranged on a certain circumference, but the plurality of LEDs 33 may be also arranged on another circumference having a different radius. As a result, the number of LEDs 33 for each wavelength increases so that it is possible to increase the amount of illumination light. In addition, the LEDs 33 for multi-spectral imaging may be arranged on a first circumference and the white LED may be arranged on a second circumference. A radius of the first circumference is different from a radius of the second circumference.

A plurality of light emitting elements that output illumination beams having the same lighting color are arranged at equal intervals in the illumination device 3. As a result, the workpiece 2 is uniformly irradiated with a plurality of illumination beams having the same lighting color. This is useful in terms of accurately generating a spectral image for multi-spectral imaging. In addition, a plurality of light emitting elements that generate illumination beams having different lighting colors, respectively, are arranged at equal intervals in each illumination block. The plurality of light emitting elements arranged in the one illumination block may also be arranged at equal intervals. As a result, the illumination beams irradiated from the plurality of illumination blocks are further uniformized. In addition, the number of the plurality of light emitting elements included in each illumination block and types of lighting colors of the plurality of light emitting elements coincide with each other. That is, the four LED boards 32 are the same parts so that management efficiency and production efficiency of the parts are improved.

<Circuit Configuration of Illumination Device>

Figure 4:
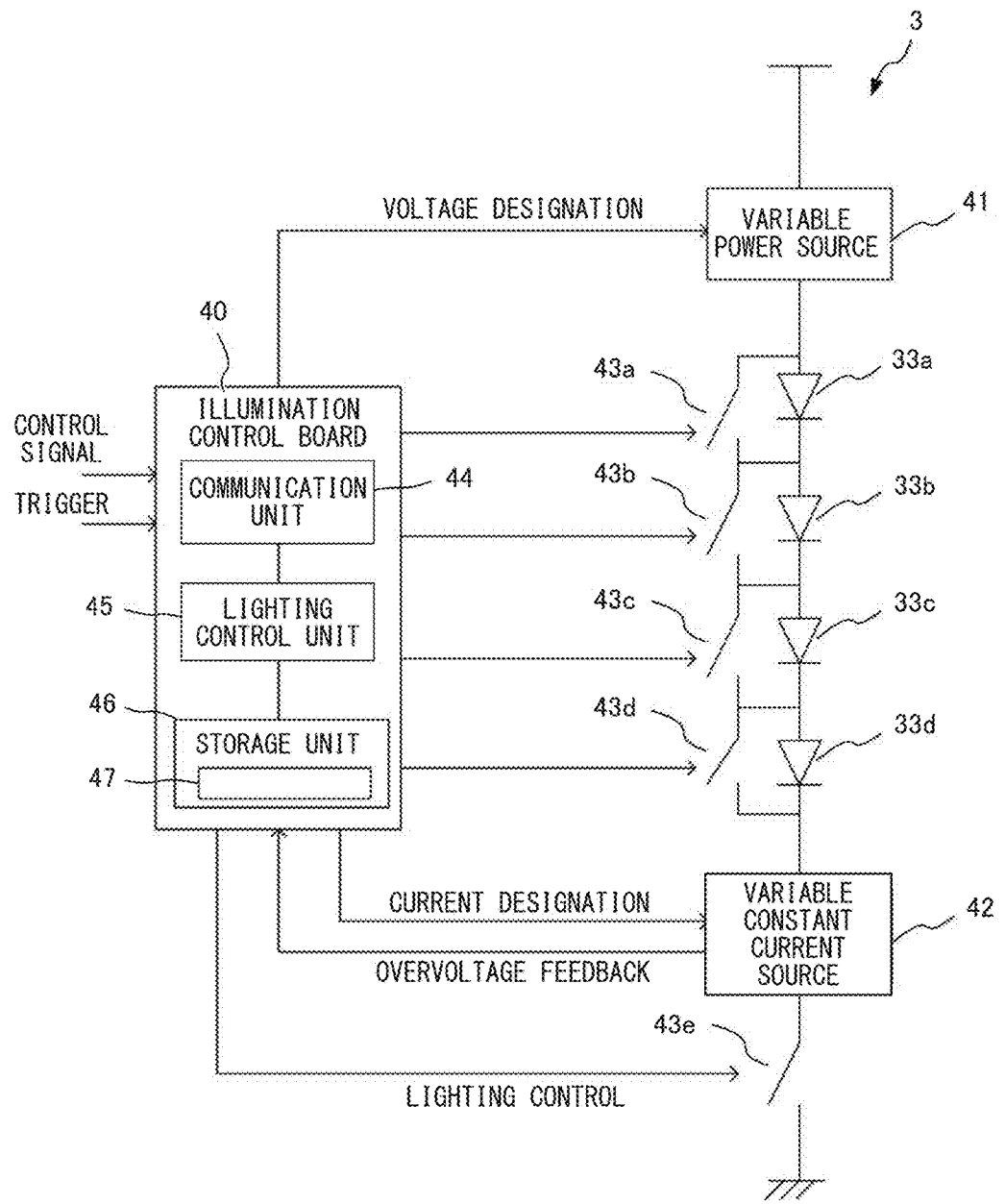
FIG. 4 is a diagram illustrating an electrical configuration of the illumination device.

FIG. 4 illustrates an example of a circuit configuration of the illumination device 3. In this example, one illumination block out of the four illumination blocks constituting the light source group is illustrated, and each illumination block is provided with four LEDs (LED 33a to LED 33d) having the same wavelength. The four LEDs 33a to 33d are connected in series. LEDs having different wavelengths connected in series in the same manner are connected in parallel with the circuit configuration of FIG. 4, but are not illustrated in FIG. 4. A variable power source 41 with a variable voltage generates and outputs a voltage having a voltage value (for example, 2 V to 20 V) designated by an illumination control board 40. A variable constant current source 42 adjusts a current flowing in the illumination block so as to have a current value (for example, 0 A to 1 A)

designated by the illumination control board 40. As such a current control system is employed, it is easy to realize dimming with high linearity. In addition, the variable constant current source 42 detects a value of a voltage applied to the variable constant current source 42 and performs feedback to the illumination control board 40, thereby protecting the variable constant current source 42 from an overvoltage. Switches 43a to 43d are connected in parallel to the LEDs 33a to 33d, respectively. A lighting control unit 45 of the illumination control board 40 can individually switch on and off of each of the LEDs 33a to 33d by individually opening and closing these switches 43a to 43d. As the switches 43a to 43d are connected in parallel to the LEDs 33a to 33d, respectively, in this manner, it is possible to perform the individual lighting by turning on any one of the LEDs 33a to 33d or turning on all of the LEDs 33a to 33d. This is useful for realizing various lighting patterns. The lighting control unit 45 executes the lighting control in the unit of one illumination block by switching on/off of a main switch 43e inserted between the variable constant current source 42 and a ground. A communication unit 44 receives a control signal to instruct a lighting pattern and a trigger signal to instruct start of lighting from an illumination control unit of the image processing device 5, and sends the signals to the lighting control unit 45. The lighting control unit 45 reads lighting pattern data 47 corresponding to the control signal from a storage unit 46 and controls the switches 43a to 43d according to the lighting pattern data 47. Eight switches 43 are provided when one illumination block is constituted by eight LEDs 33, and the eight switches 43 are controlled by the lighting control unit 45.

<Functional Block>

Figure 5:
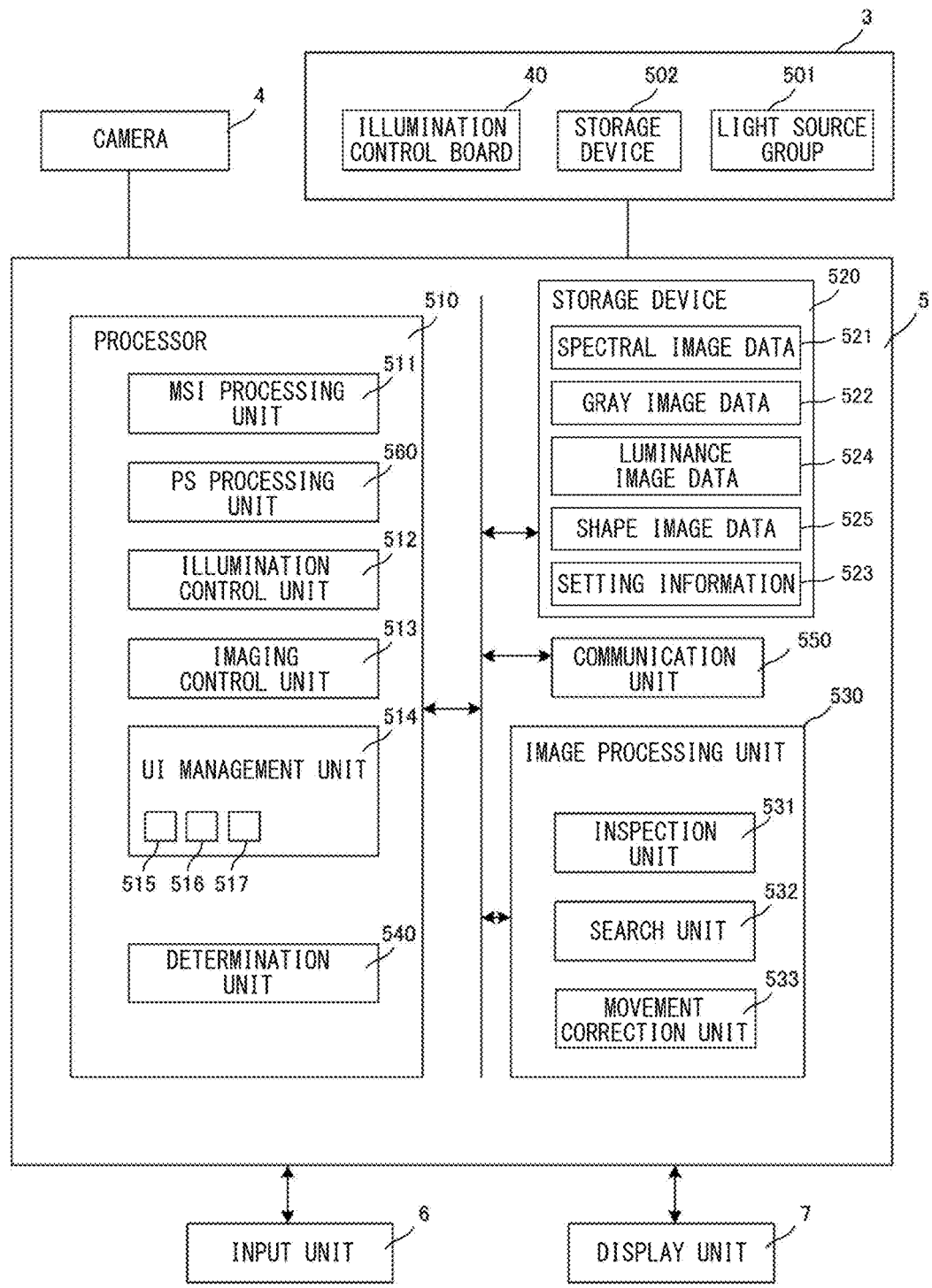
FIG. 5 is a diagram illustrating functions of an image processing system.

FIG. 5 is a block diagram of an inspection device. In this example, the illumination device 3, the camera 4, and the image processing device 5 are housed in individual casings, respectively, but this is merely an example, and the integration thereof may be obtained as appropriate. The illumination device 3 is the illumination device that realizes the multi-spectral imaging, but may be used as an illumination section that illuminates an inspection target object according to a photometric stereo method. The illumination device 3 includes a light source group 501 and the illumination control board 40 that controls the light source group 501. As already illustrated in FIGS. 3A to 3E, one illumination block may be constituted by the plurality of light emitting elements, and the light source group 501 may be constituted by the plurality of illumination blocks. The number of illumination blocks is generally four, but may be three or more. This is because it is possible to generate an inspection image by the photometric stereo method if the workpiece 2 can be irradiated with illumination beams from three or more illumination directions. Each illumination block is provided with the plurality of light emitting elements (LEDs 33) that output illumination beams having different wavelengths, respectively. The plurality of light emitting elements may include the white LED. The white LED is not used for the multi-spectral imaging but can be used to create another inspection image and to create an image for movement correction of the workpiece 2. As illustrated in FIGS. 1 and 3A to 3E, an outer shape of the illumination device 3 may have a ring shape. In addition, the illumination device 3 may be constituted by a plurality of illumination units separated from each other. The illumination control board 40 controls a lighting timing and an illumination pattern (lighting pattern) of the light source group 501 according to a control command received from the image processing device 5. The workpiece 2 is irradiated with illumination beams of alternately selected wavelengths when acquiring the spectral image by the multi-spectral imaging, but may be irradiated simultaneously with the illumination beams of a plurality of lighting colors (wavelengths) when a method other than the multi-spectral imaging is adopted. The illumination control board 40 has been described as being built in the illumination device 3, but may be built in the camera 4 or the image processing device 5, or may be housed in a casing independent therefrom.

A storage device 502 is built in the illumination device 3, and the lighting timing and the illumination pattern of the light source group 501 set by the user are stored therein. The illumination control board 40 can receive the trigger signal from the image processing device 5 and control the light source group 501 according to contents stored in the storage device 502. With this configuration, the image processing device 5 can control the illumination device 3 only by transmitting the trigger signal, and thus, it is possible to reduce the number of signal lines that connect the image processing device 5 and the illumination device 3, thereby improving the handling of cables.

More specifically, the storage device 502 stores illumination setting data that includes lighting timing information (a lighting time and a lighting interval), illumination intensity information, illumination pattern information (identification information of a wavelength to be turned on), and illumination block information (identification information of a block to be turned on) of the light source group 501 of each wavelength. All of the illumination setting data causes the user interface for illumination setting to be displayed on the display unit 7, and an illumination setting section receives adjustment made by the user.

The lighting timing information is information that defines a lighting timing of each wavelength when the light source group corresponding to each wavelength is periodically turned on, and includes the lighting time (pulse width) in which the light source group of each wavelength is turned on, and the lighting interval (interval) from turning-on of the light source group of a previous wavelength to turning-on of the light source group of a next wavelength at the time of switching the wavelength to be turned on. For example, when the user performs inspection using a light source group emitting red and green light, the user can set a lighting time of the light source group of a red wavelength, a lighting time of the light source group of a green wavelength, and an interval between both the lighting times. The user may individually set the lighting time of each wavelength, or the setting of the lighting time may be common to the entire wavelength. Regarding the setting of the lighting interval, the user may directly designate the lighting interval, or the lighting interval may be automatically calculated based on a length of one lighting cycle for sequentially turning on the light source group of the entire wavelength used for inspection and the lighting time of each wavelength.

The illumination intensity information is information that indicates the illumination intensity of each wavelength. The illumination intensity of each wavelength can be individually set in the present embodiment, and thus, it is possible to irradiate the workpiece with light with an optimum illumination intensity at each wavelength.

The illumination pattern information is identification information that indicates a type of the wavelength to be turned on, and is information used to decide which light source group corresponding to which wavelength needs to be turned on at each lighting timing. For example, when the user performs setting of inspection using three colors of red, green, and purple, the storage device 502 stores the identification information indicating these three wavelengths in association with the information on each lighting timing (lighting pulse). For example, the storage device 502 stores the illumination pattern information in association with the lighting timing information such that a red light source group is turned on with a first lighting pulse, a green light source group is turned on with a next lighting pulse, and a purple light source group is turned on with a last lighting pulse. Information indicating an order of lighting wavelengths may be included in the illumination pattern information. In the above example, the order of red, green, and purple may be set by the user, or a lighting order of wavelengths that can be set may be fixed and determined in advance. A storage device 520 of the image processing device 5 shares the illumination pattern information with the illumination device 3. In the above example, an image acquired first is processed as an image obtained with a red wavelength, an image acquired next is processed as an image obtained with a green wavelength, and an image acquired last is processed as an image obtained with a purple wavelength.

The illumination block information is identification information on the illumination block to be turned on. In the present embodiment, it is possible to individually control lighting in units of illumination blocks as well as to individually control lighting in units of wavelengths. The user can execute inspection using oblique illumination by arbitrarily selecting the illumination block to be turned on. In addition, it is also possible to generate a shape image using the principle of photometric stereo based on a plurality of luminance images obtained by illuminating light from different illumination directions by sequentially turning on all the illumination blocks. The user can also set an order of illumination blocks to be turned on. Illumination block to be turned on may be arbitrarily designated at each lighting timing, or a rotation direction of lighting (clockwise or counterclockwise) may fixed such that the user can designate an illumination block to be turned on first.

The illumination setting data set by the illumination setting section may be set from an input unit such as a personal computer (PC) connected to the illumination device 3 or from the image processing device 5 connected to the illumination device 3. In addition, the illumination device 3 may receive the setting via a controller for illumination which is provided separately from the image processing device 5. In addition, it is also possible to directly perform the illumination setting in an inspection device via the input unit 6 in the case of the inspection device in which the camera 4, the illumination device 3, and the image processing device 5 are integrally provided.

The storage device 502 is provided in the illumination device 3 in the above example, but may be provided in the image processing device 5. In addition, the storage device 502 may be provided in the camera 4 when the illumination device 3 and the camera 4 are integrally provided. When the illumination device 3, the camera 4, and the image processing device 5 are integrally provided in one housing, the storage device 502 is provided in the housing.

The camera 4 is an example of the imaging section that receives light reflected from the inspection target object illuminated by the illumination device 3 and generates the luminance image, and executes imaging processing according to the control command from the image processing device 5. The camera 4 may create a luminance image of the workpiece 2 and transfer the created luminance image to the image processing device 5, or a luminance signal obtained from an imaging element of the camera 4 may be transferred to the image processing device 5 so that the image processing device 5 may generate a luminance image. Since the luminance image is based on the luminance signal, the luminance signal is also the luminance image in a broad sense. In addition, the camera 4 functions as the imaging unit that receives the light reflected from the target object for each of illumination beams of the respective wavelengths output from the illumination device 3 and generates the image (spectral image) of the target object.

The image processing device 5 is a type of computer, and includes a processor 510 such as a CPU and an ASIC, the storage device 520 such as a RAM, a ROM, and a portable storage medium, an image processing unit 530 such as an ASIC, and a communication unit 550 such as a network interface. The processor 510 performs setting of an inspection tool, adjustment of the control parameter, generation of the inspection image, and the like. In particular, an MSI processing unit 511 creates a gray image of the workpiece 2 from a plurality of luminance images (spectral images) acquired by the camera 4 or creates an inspection image by performing image processing (for example, binarization and the like) on the gray image according to multi-spectral imaging (MSI). The gray image itself may be the inspection image. An illumination control unit 512 controls the lighting pattern, an illumination switching timing, and the like by transmitting the control command to the illumination control board 40. That is, the illumination control unit 512 transmits a trigger signal to start illumination to the illumination device 3. An imaging control unit 513 transmits a trigger signal to start imaging in synchronization with the trigger signal issued from the illumination control unit 512 to the camera 4, thereby controlling the camera 4.

A UI management unit 514 displays a user interface (UI) for setting of the inspection tool, a UI for setting of a parameter required to generate the inspection image, and the like on the display unit 7, and sets the inspection tool and the parameter according to the information input from the input unit 6. The inspection tool may include a tool to measure a length of a specific characteristic (for example, a pin) provided in the workpiece 2, a tool to measure the area of the characteristic, a tool to measure a distance from a certain characteristic to another characteristic (for example, a pin interval) from one characteristic to another, a tool to measure the number of specific characteristics, a tool to inspect whether there is a flaw on a specific characteristic, and the like. In particular, the UI management unit 514 displays a UI for setting of a control parameter relating to multi-spectral imaging and movement correction on the display unit 7. An image selection unit 515 reads image data of an image selected by the user through the UI from the storage device 520 and displays the image in an image display region inside the UI. A region designation unit 516 receives designation of an inspection region IW of the inspection tool, a pattern region PW configured to register a characteristic pattern for movement correction and position correction, a search region SW, and the like from the user with respect to the displayed image. In addition, the region designation unit 516 receives selection of shapes (for example, a rectangle, a circle, an ellipse, or an arbitrary shape) of these designation regions and reflects a shape of a frame line indicating the designation region to the UI. A lighting color setting unit 517 sets a lighting color of an illumination beam for movement correction according to the user's instruction. The UI management unit 514 saves these control parameters set by the user in setting information 523. In this manner, the UI management unit 514 functions as a setting unit that sets an illumination condition and an imaging condition or as a setting unit that sets the inspection tool.

The image processing unit 530 includes an inspection unit 531, which executes various types of measurement by applying the inspection tool to the inspection image acquired by the multi-spectral imaging, and the like. A search unit 532 searches for a characteristic set before image inspection or a characteristic dynamically set during the image inspection within a search region SW arranged in the inspection image, and obtains a position of the found characteristic. The inspection unit 531 corrects a position of the inspection region (measurement region) according to the position of the found characteristic. A movement correction unit 533 corrects a coordinate system of a plurality of spectral images for multi-spectral imaging or coordinates (position) of the workpiece 2 based on the change amount of the position of the characteristic found from the image for movement correction. This correction work may be divided into a step of creating a conversion formula (correction formula) for correction and a step of converting coordinates using the conversion formula. Both of these two processes may be executed by the movement correction unit 533, the former process may be executed by the movement correction unit 533 and the latter process may be executed by the MSI processing unit 511, or both of the processes may be executed by the MSI processing unit 511. The function of the image processing unit 530 may be implemented on the processor 510. Alternatively, the function of the processor 510 may be implemented on the image processing unit 530. In addition, the processor 510 and the processor 510 may implement a single function or a plurality of functions in cooperation with each other. For example, the image processing unit 530 may perform a part of the calculation relating to movement correction, and the processor 510 may perform the remaining calculation. The movement correction unit 533 may correct a coordinate system of a plurality of luminance images (direction images) for photometric stereo or coordinates (position) of the workpiece 2 based on the change amount of the position of the characteristic found from the image for movement correction.

A determination unit 540 functions as a determination section for determining whether the workpiece 2 is non-defective/defective using the inspection image. For example, the determination unit 540 receives a result of the inspection performed using the inspection image in the image processing unit 530 and determines whether the inspection result satisfies a non-defective product condition (the tolerance or the like).

The storage device 520 stores spectral image data 521 which is data of the spectral image acquired by the camera 4, gray image data 522 which is data of the gray image generated by the MSI processing unit 511, and the setting information 523 holding the various control parameters. In addition, the storage device 520 also stores various types of setting data, a program code for generating the user interface, and the like. The storage device 520 may also store and hold the inspection image generated from the gray image and the like. The storage device 520 may store luminance image data 524 which is data of the direction image (luminance image) acquired by the camera 4 and shape image data 525 which is a shape inspection image created from the luminance image.

Figure 22:
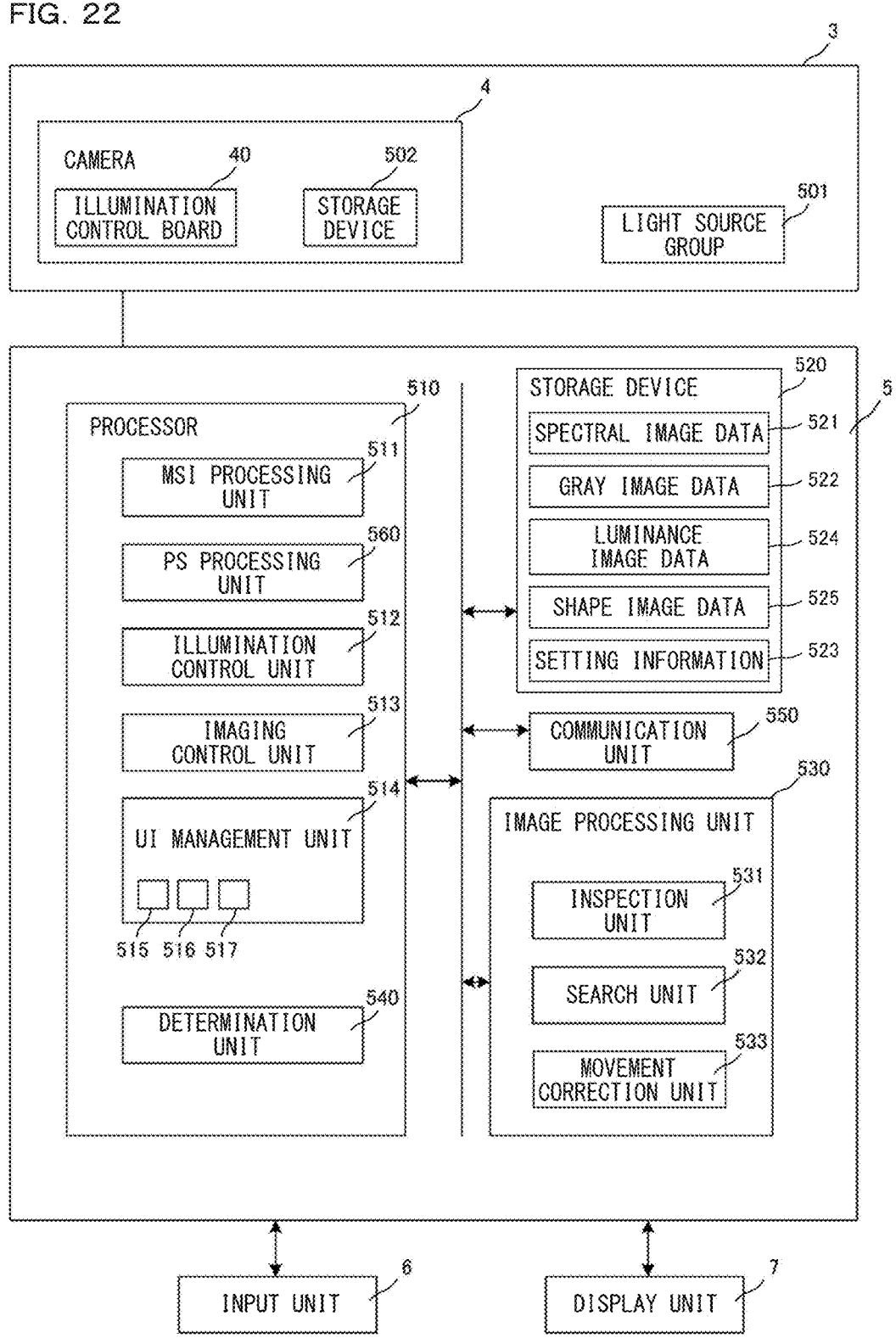
FIG. 22 is a diagram illustrating functions of an image processing system.
Figure 23:
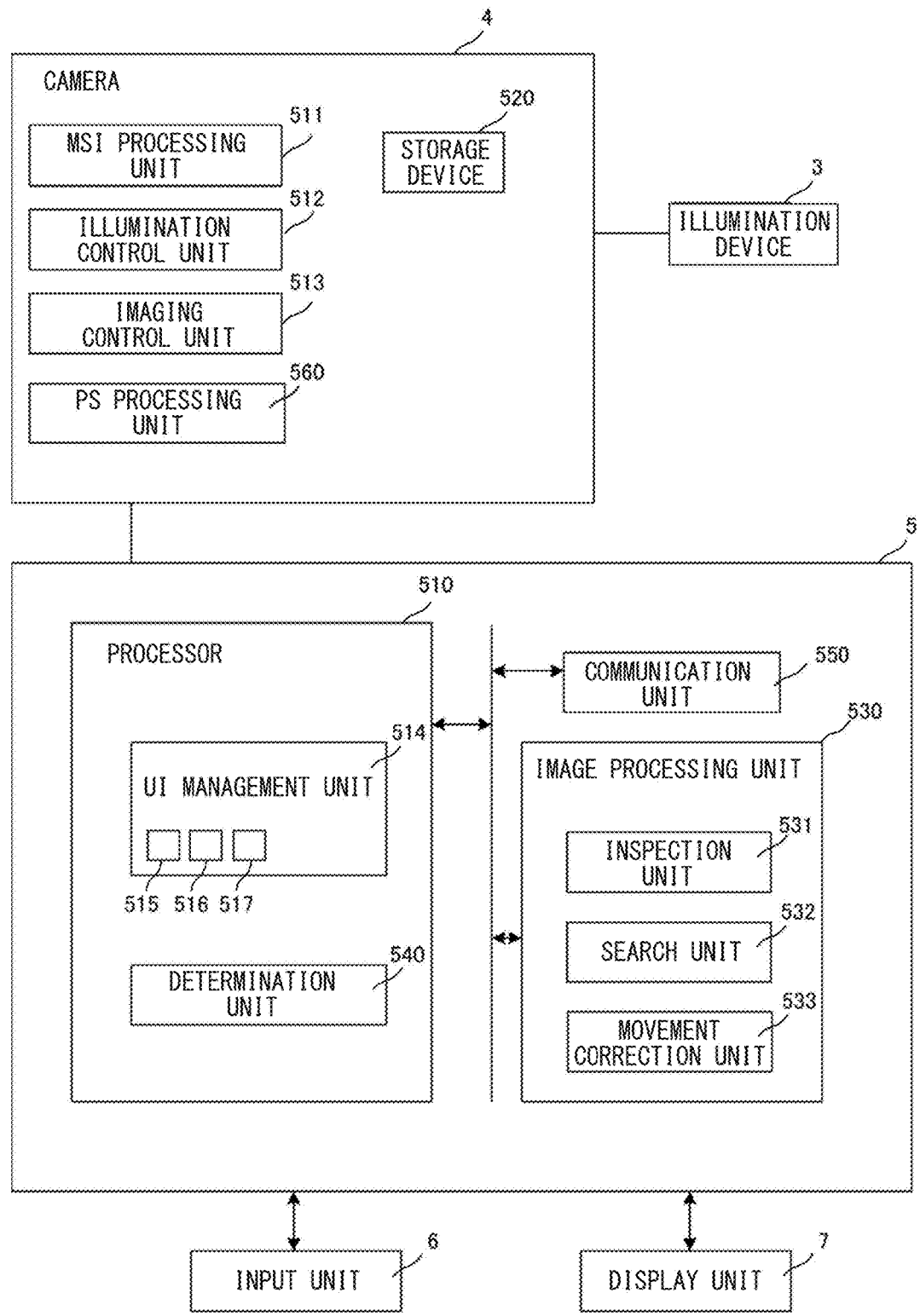
FIG. 23 is a diagram illustrating functions of an image processing system.
Figure 24:
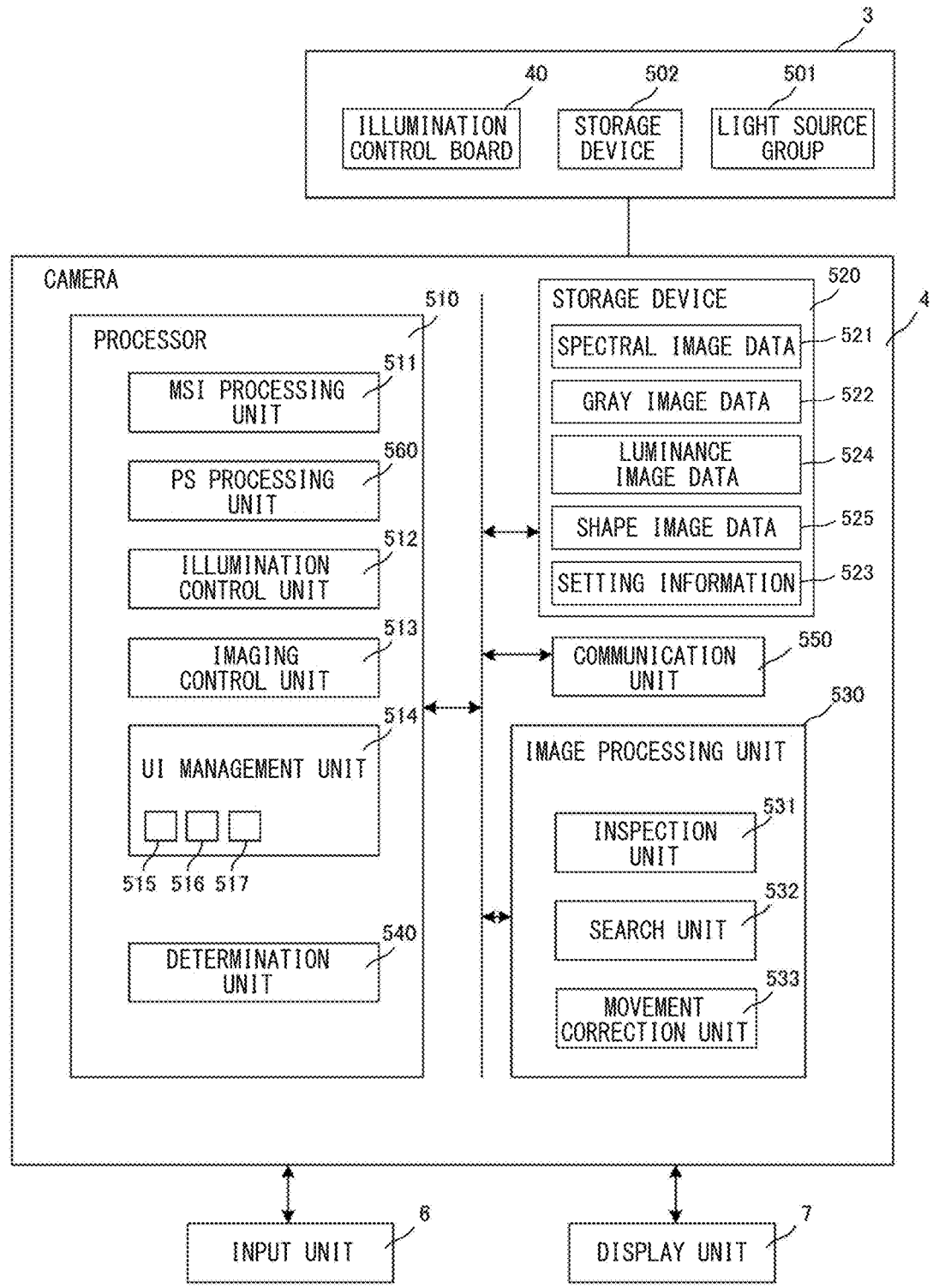
FIG. 24 is a diagram illustrating functions of an image processing system.

FIGS. 22 to 24 are diagrams illustrating another configuration example of the image processing device of the present invention. FIG. 22 is the diagram illustrating an example in which the illumination device 3 and the camera 4 are integrated, and the illumination control board 40 configured to control the illumination device 3 is provided in the camera 4. Since the illumination device 3 and the camera 4 are integrally provided in this configuration, it is not necessary to perform positioning at the time of installing the illumination device 3 and the camera 4. In addition, the illumination control board 40 configured to control the light source group 501 and the storage device 502 are unnecessary on the illumination device 3 side, and the general-purpose illumination device 3 that does not include the illumination control board 40 and the storage device 502 can also be used. The user can remove the illumination device 3 connected to the camera 4 and replace the illumination device 3 with another type of illumination device. For example, it is possible to appropriately select other types of illumination devices, such as a ring illumination that emits only white light, instead of the illumination device 3 used for the multi-spectral imaging in the present invention. It is preferable that the camera 4 recognize the type of the connected illumination device 3 and reflect the type on the setting user interface. Accordingly, the user can perform the illumination setting on the user interface corresponding to an item that can be set in the connected illumination device 3. A method in which the illumination device 3 stores illumination type information and the camera 4 refers to the information is conceivable as a method of recognition. In addition, the illumination control unit 512 and the imaging control unit 513 included in the image processing device 5 may be provided inside the camera 4, and control of an imaging and illumination system may be executed independently from the image processing device 5.

FIG. 23 illustrates the configuration example in which some functions of the image processing device 5 are provided on the camera 4 side. The camera 4 includes the storage device 502 that stores the spectral image data 521, the gray image data 522, and the setting information 523, the luminance image data 524, and the shape image data 525, and the MSI processing unit 511 executes the process of generating the gray image data 522 from the spectral image data 521 inside the camera 4. A PS processing unit 560 creates the shape image data 525 based on the luminance image data 524. The illumination device 3 is controlled by the illumination control unit 512 of the camera 4. At the time of inspection setting, the camera 4 transmits the spectral image data 521 captured at each wavelength to the image processing device 5 and the gray image data 522 generated by the MSI processing unit 511 to the image processing device 5. At the time of setting, the image processing device 5 acquires the spectral image data 521 from the camera 4 and displays the acquired data on the display unit 7, so that the user can confirm the illumination intensity of each wavelength and whether the spectral image data 521 of each wavelength is necessary for inspection. On the other hand, at the time of inspection operation, only the gray image data 522 to be inspected may be transmitted to the image processing device 5 without transmitting the spectral image data 521 from the camera 4 to the image processing device 5. As the camera 4 is caused to have some functions of the image processing device 5 in this manner, a communication load between the camera 4 and the image processing device 5 is reduced, and the speed of processing increases due to distributed processing. When the movement correction is applied at the time of creating the gray image data 522 and the shape image data 525, the search unit 532 and the movement correction unit 533 may also be provided in the camera 4.

FIG. 24 is the configuration example in which all functions of the image processing device 5 are incorporated in the camera 4. It is sufficient for the user to install only the camera 4 and the illumination device 3, and thus, little time and effort is required at the time of installation. For example, this configuration may be advantageous when the camera 4 is allowed to have a large size and advanced image processing is unnecessary.

<Multi-Spectral Imaging>

In the multi-spectral imaging, the workpiece 2 is irradiated sequentially with illumination beams having different lighting colors (wavelengths) one by one, and an image for each wavelength is acquired. For example, eight images (spectral images) are acquired in the case of irradiation with illumination beams of eight types of wavelengths. When there are four illumination blocks, the four illumination blocks are turned on at the same time. That is, since the four LEDs 33 of the same wavelength are simultaneously turned on, the workpiece 2 is irradiated with the illumination beams of the same wavelength from four directions.

For example, the eight types of wavelengths are eight narrow-band wavelengths from an ultraviolet wavelength to a near-infrared wavelength. The narrow-band wavelength refers to a wavelength narrower than a width of a wavelength (wide-band wavelength) of light emitted by the white LED. For example, a width of a wavelength of light emitted by a blue LED is much narrower than the wavelength width of the light emitted by the white LED, and thus, the wavelength of the light emitted by the blue LED is the narrow-band wavelength. In the image inspection, there may be image inspection that does not require all of the eight spectral images. In this case, the workpiece 2 is irradiated with only an illumination beam of a necessary wavelength.

In general, it is unlikely that the eight images are directly used for image inspection, one gray image is created from the eight images (color gray-scale conversion), and this gray image (color gray-scale image) is used for the image inspection.

The color gray-scale conversion is sometimes called color-gray conversion. For example, binarization processing is executed on the color gray-scale image, edge detection processing is executed, or blob processing is executed so that whether a position, a size (a length or area) and a color of a characteristic (for example, a pin) in the workpiece 2 fall within tolerance ranges, respectively, are inspected.

Figure 6:
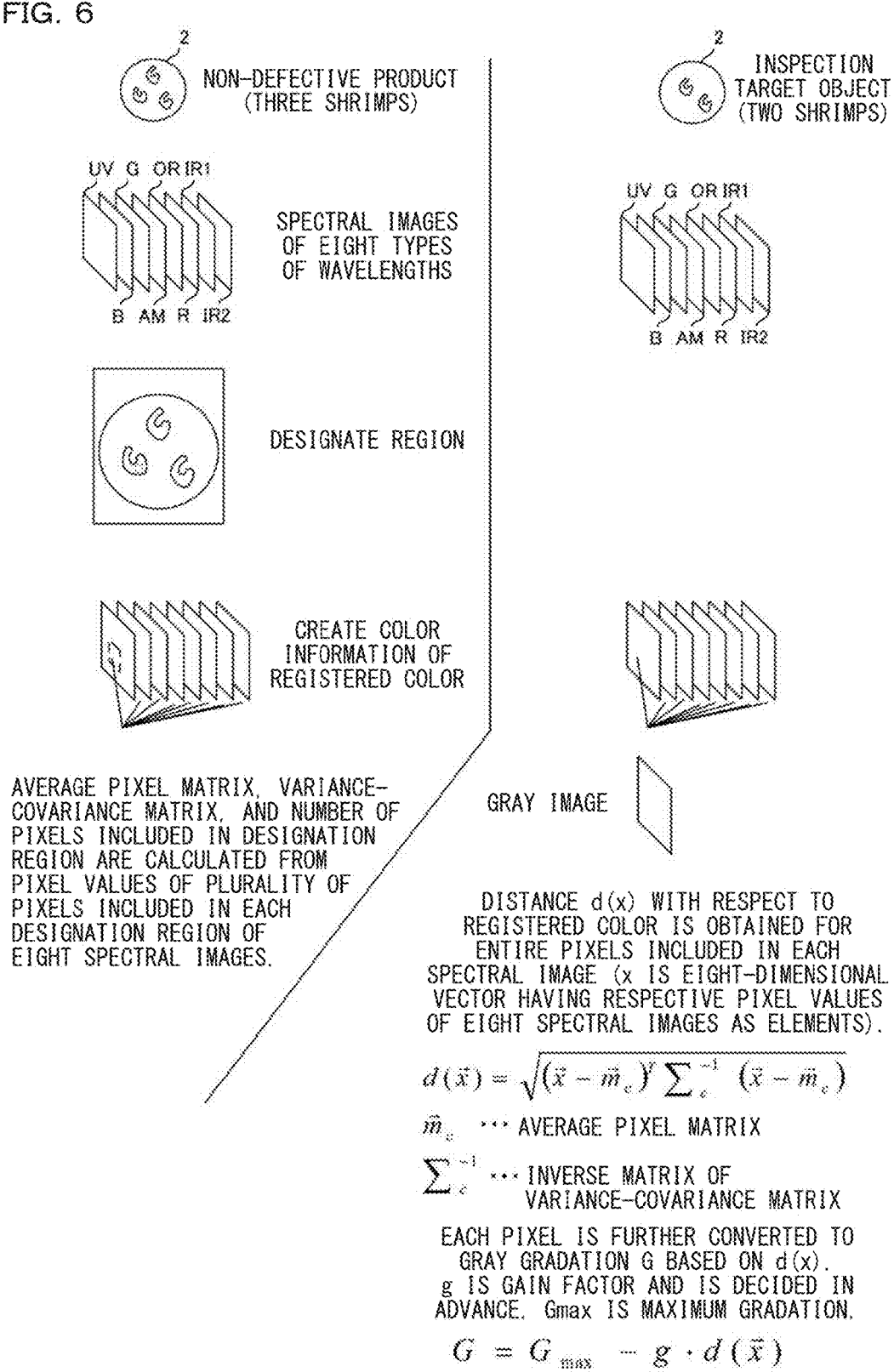
FIG. 6 is a view illustrating a principle of color gray-scale conversion in multi-spectral imaging.

An example of the color gray-scale conversion will be described with reference to FIG. 6. When creating the gray image of the workpiece 2 which is the inspection target object, a registered color of a non-defective product (model) is required. This is because the gray image is created by converting the eight spectral images using color information of the registered color as a reference.

First, in a setting mode, the color information of the registered color is extracted from an image region (designation region) designated by the user in the eight spectral images acquired from the non-defective product.

For example, when the non-defective product is an instant food (for example, Chinese noodle) and the number of certain ingredients (for example, shrimps) is counted by image inspection, the user displays an image of the non-defective product and designates a rectangular designation region including the ingredient in the non-defective product image, and the color information of the registered color is extracted from pixels included in the designation region. The color information of the registered color includes an average pixel matrix, a variance-covariance matrix, and the number of the pixels included in the designation region. The color information may be extracted by a so-called dropper tool. An UI of the dropper tool may be implemented on the region designation unit 516.

Next, eight spectral images are acquired for the workpiece 2 as the inspection target object in the inspection mode. A distance d(x) with respect to the registered color is obtained for all pixels included in each spectral image (x is an eight-dimensional vector having the respective pixel values of the eight spectral images as elements). Further, a product is obtained by multiplying the distance d(x) by a predetermined gain g, an offset a is added if necessary, and a difference G obtained by subtracting the product from a maximum gradation Gmax that each pixel can take becomes a gray gradation of a pixel x of interest. This is expressed as G=Gmax−(g·d(x)+a).

When there are a plurality of registered colors, a plurality of gray images may be created using each registered color as a reference, or a single gray image may be created.

<Principle of Photometric Stereo>

Figures 7A, 7B, 7C:
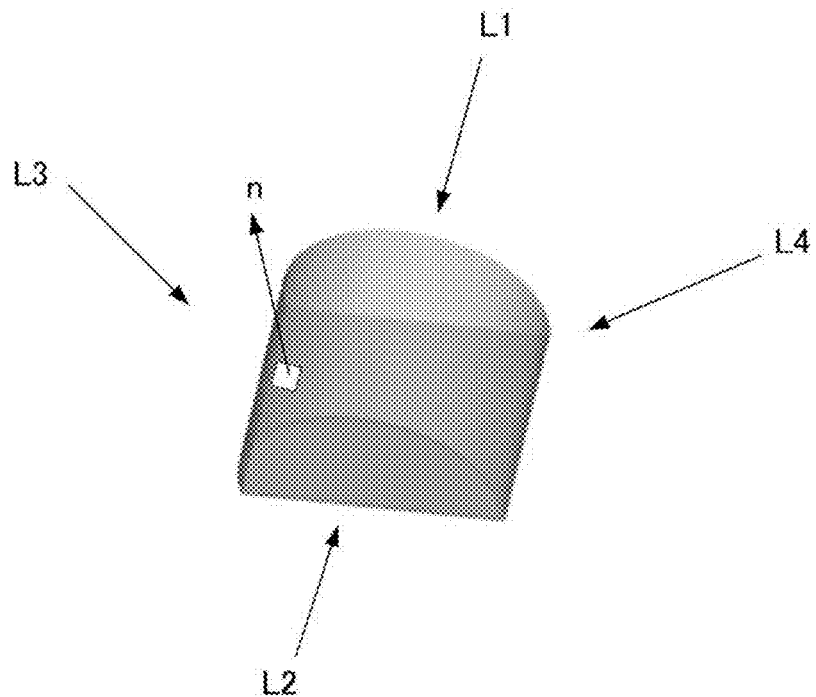
FIG. 7A to 7C is a view for describing a principle of photometric stereo.

In a general photometric stereo method, the workpiece 2 is irradiated sequentially with illumination beams L1 to L4 from the four directions in a switching manner, thereby generating four luminance images as illustrated in FIG. 7A. The four luminance images may be referred to as direction images because the illumination directions thereof are different from each other. A direction of an illumination beam used when photographing each luminance image is only one direction. A luminance image is constituted by a plurality of pixels, and four pixels whose coordinates coincide with each other in four luminance images correspond to the same workpiece surface. Equation 1 illustrated in FIG. 7B is established among pixel values (luminance values) I1, I2, I3, and I4 of the four pixels and a normal vector n.

Here, ρ is a reflectance. L is a known light amount of illumination beams from each direction. Here, the light amount is the same in all the four directions. S is a known illumination direction matrix. The reflectance p and the normal vector n for each coordinate (workpiece surface) are obtained by solving this mathematical formula. As a result, a reflectance image (albedo image) and an inclination image are obtained.

In the present embodiment, a height component is further extracted from the inclination image, and a shape image representing the shape of the workpiece 2 is created as an inspection image. The inspection image is obtained by an integral equation which is Equation 2 illustrated in FIG. 7C. Here, zn is the n-th integral result and represents a shape of the workpiece surface. Further, x and y represent coordinates of a pixel. Further, n represents the number of times of repetitive calculation. Further, p represents an inclination component in the horizontal direction, and q represents an inclination component in the vertical direction. Further, p and q are obtained from the normal vector n. Further, w is a weight. In addition, a 1/1 inclination image is used in the first integral calculation, a ½-reduced inclination image is used in the second integral calculation, and a ¼-reduced inclination image is used in the third integral calculation. When creating a reduced image, reduction processing may be performed after performing Gaussian processing.

Figure 8:
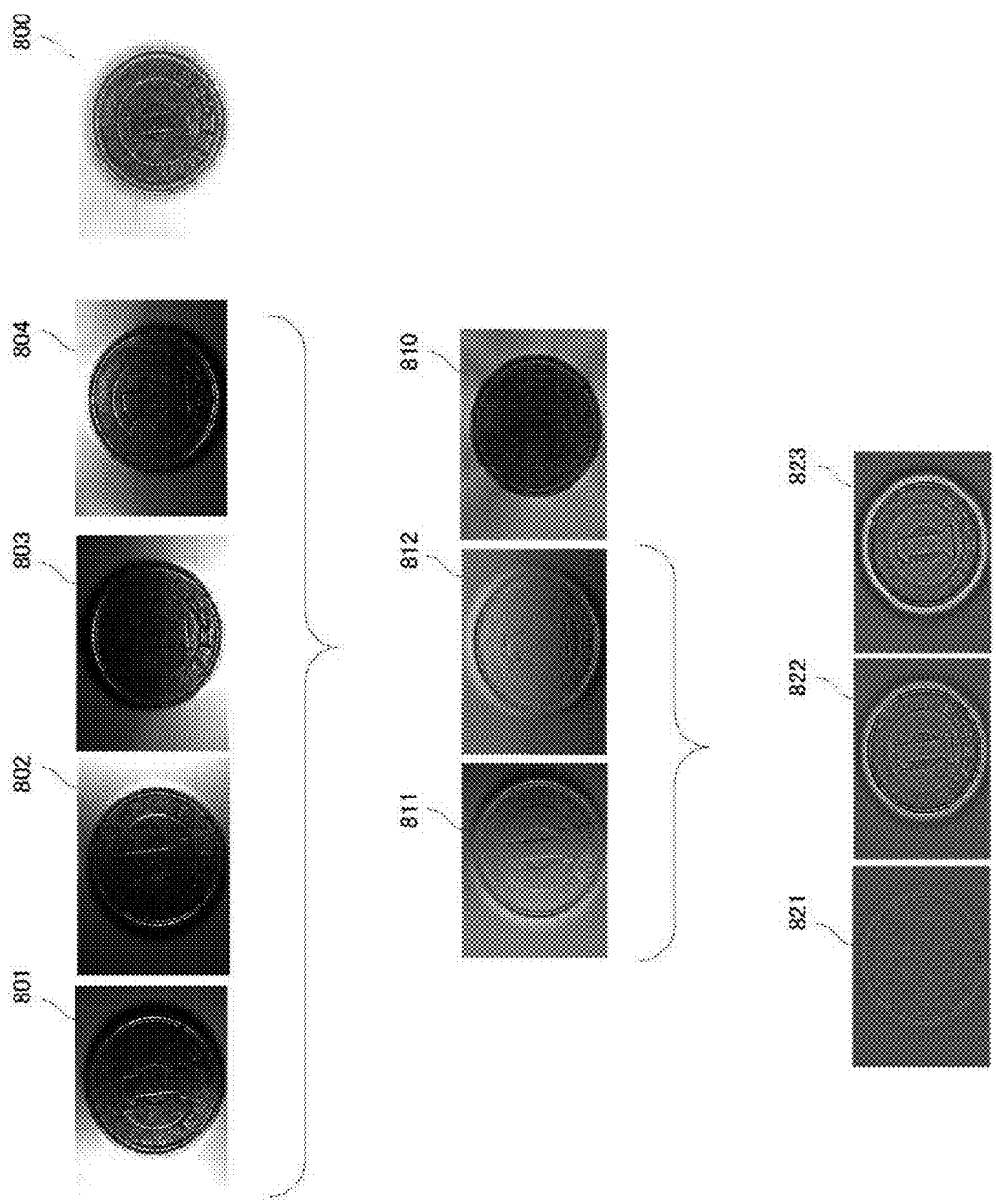
FIG. 8 is a view for describing the principle of photometric stereo.

FIG. 8 is a view illustrating a process of creating the inspection image by the photometric stereo method. Luminance images 801 to 804 are luminance images acquired by illuminating the workpiece 2 with illumination beams having different illumination directions, respectively. A luminance image 800 is a luminance image obtained by simultaneous illumination from the four directions. The normal vector of the workpiece surface is obtained by calculation using the plurality of luminance images obtained by illuminating the workpiece 2 with the illumination beams having different illumination directions, respectively. An inclination image 811 is an inclination image in which inclination components in the X direction of the normal vector obtained from the luminance images 801 to 804 are taken as pixel values. An inclination image 812 is an inclination image in which inclination components in the Y direction of the normal vector obtained from the luminance images 801 to 804 are taken as pixel values. A reflectance image 810 is a reflectance image in which a variation of a brightness value caused by an inclination of the workpiece surface is removed from the normal vector obtained from the luminance images 801 to 804 and the reflectance of the workpiece surface is taken as an image. Inspection images 821 to 823 are images (surface shape images) which have different characteristic sizes, respectively, and are obtained from the inclination images 811 and 812. The inspection images 821 to 823 are also constituted by pixels based on inclination components, and thus, correspond to a type of inclination images. According to this procedure, the inspection image of the workpiece 2 is generated. The luminance image 800 or the reflectance image 810 which is an omni-directional illumination image may be adopted as the inspection image depending on an inspection tool. The omni-directional illumination image is a luminance image acquired by turning on all of the plurality of light sources provided in the illumination device 3.

<Texture Information>

Figure 9:
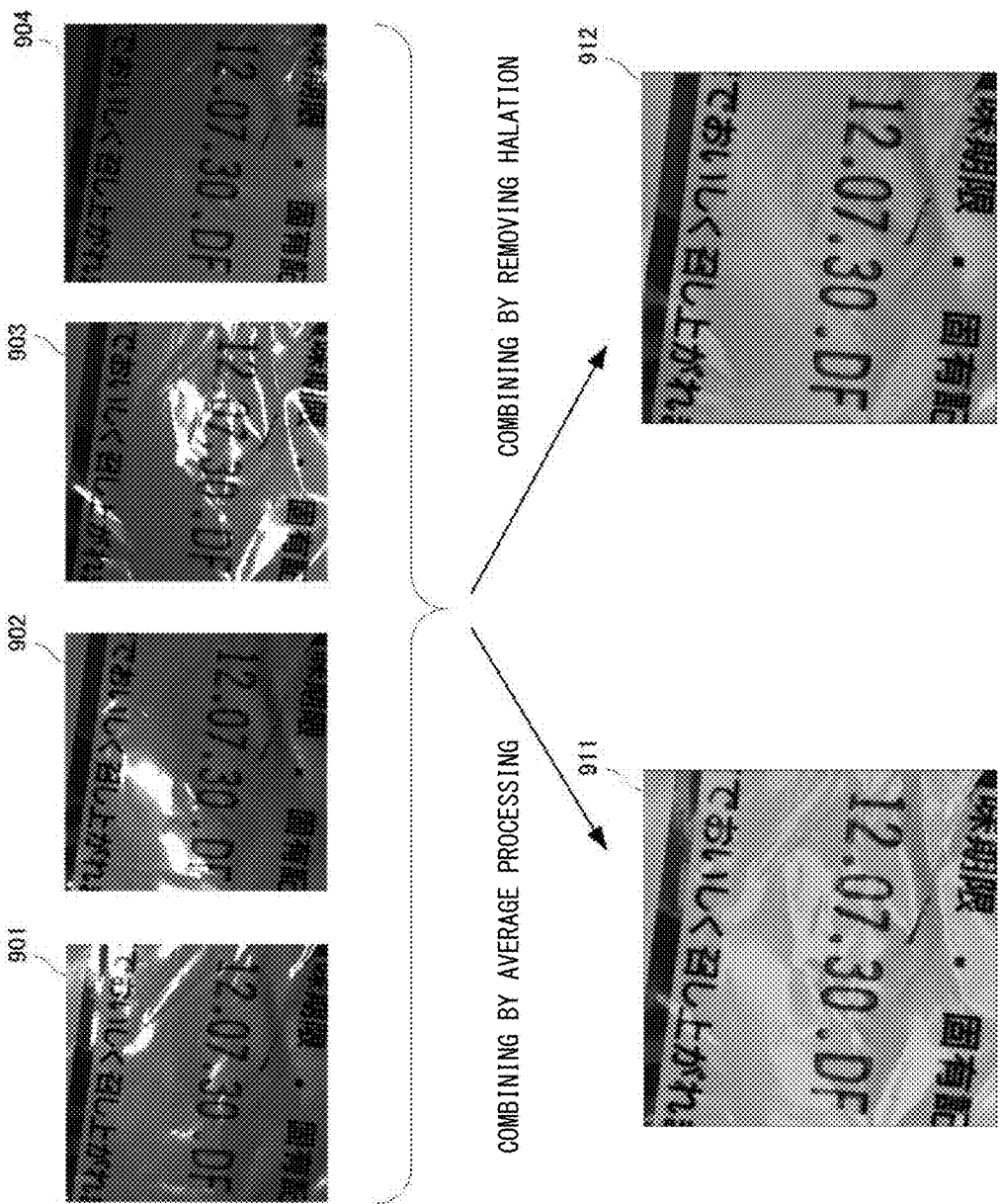
FIG. 9 is a view for describing the principle of photometric stereo.

Texture information is information based on the reflectance p of the surface of the workpiece 2. The reflectance p is obtained by Equation 1, that is, one reflectance image is obtained from four luminance images. The reflectance image is an image having a pixel value proportional to the reflectance p of the workpiece surface. As illustrated in FIG. 9, a normal vector is calculated from four luminance images 901 to 904, and pixel values proportional to reflectances of the respective pixels are calculated based on the calculated normal vector and luminance values of pixels corresponding to the plurality of luminance images, respectively, thereby obtaining texture images 911 and 912 which are reflectance images. Examples of such a combining method include a method of obtaining a texture image by pixel average of four luminance images and a method of obtaining a texture image by removing halation from four luminance images and performing pixel average. The texture image 911 is obtained by image average, and the texture image 912 is obtained by halation removal. There are four pixels whose coordinates coincide with each other in the four luminance images. It is possible to remove the halation by excluding a pixel having the largest pixel value among the four pixels or excluding pixels from the first to the N-th (N is a natural number of three or less) in descending order of pixel values. This is because the halation appears in an image as high luminance. Both the texture images 911 and 912 are constituted by pixels based on the reflectance, and thus, correspond to a type of reflectance images (albedo images).

<Setting Mode>

Figure 10:
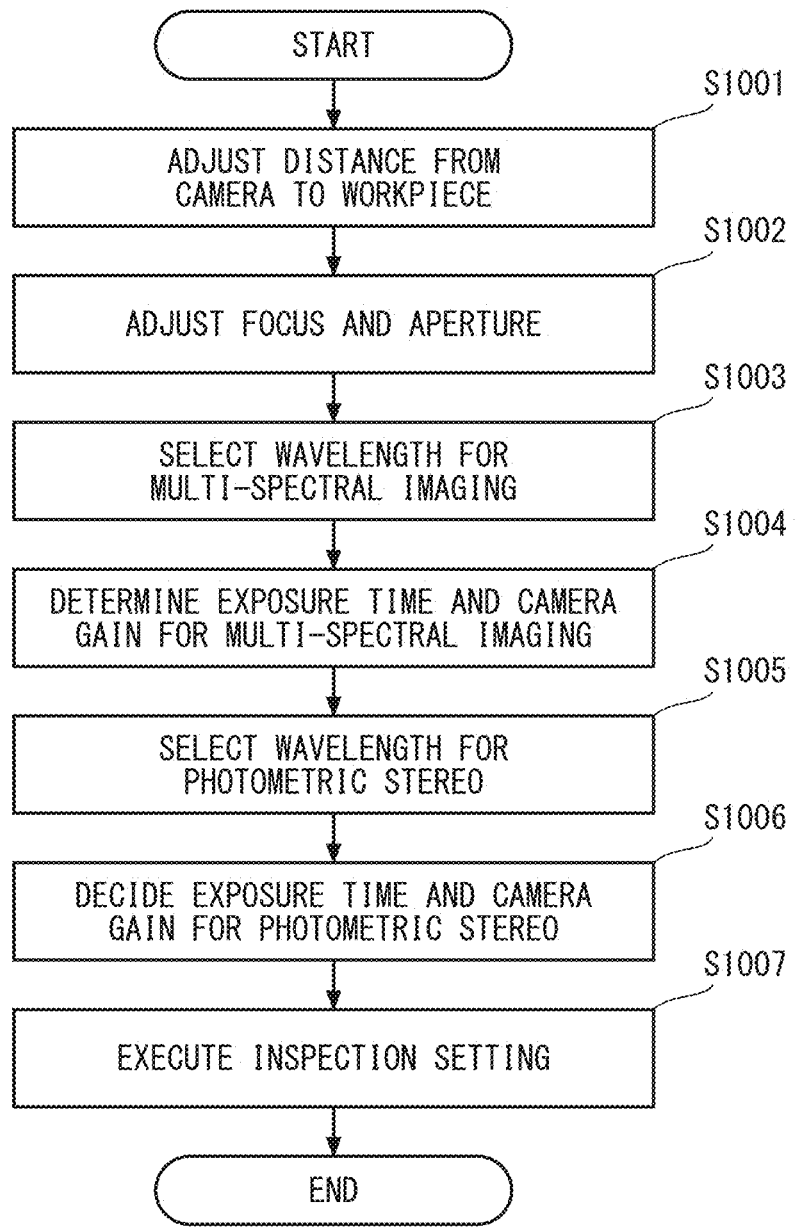
FIG. 10 is a flowchart illustrating a setting procedure relating to image inspection.

FIG. 10 illustrates a setting procedure of the image inspection device 8. In S1001, the user adjusts a distance from the camera 4 to the workpiece 2 by adjusting a fixed position of the camera 4. The UI management unit 514 may assist the user by displaying a real-time image acquired by the camera 4 on the display unit 7. In S1002, the user adjusts a focus and an aperture of the camera 4. The imaging control unit 513 may execute the focus adjustment using an auto-focus function of the camera 4. The UI management unit 514 may receive an aperture value designated by the user and set the received aperture value in the imaging control unit 513. The aperture value at this stage is a temporary value, and a final aperture value is decided at the time of adjusting an exposure time. In S1003, the user selects a lighting color for multi-spectral imaging. The UI management unit 514 (the lighting color setting unit 517) may display candidates of selectable lighting colors on the display unit 7 and receive selection of the lighting color performed by the user. For example, several lighting colors can be selected from eight lighting colors from UV to IR2. UV represents a spectral image acquired by an illumination beam of an ultraviolet lighting color. B represents a spectral image acquired by an illumination beam of a blue lighting color. G represents a spectral image acquired by an illumination beam of a green lighting color. AM represents a spectral image acquired by an illumination beam of an amber lighting color. OR represents a spectral image acquired by an illumination beam of an orange lighting color. R represents a spectral image acquired by an illumination beam of a red lighting color. IR1 and IR2 represent spectral images acquired by illumination beams of infrared lighting colors. Here, the lighting color of IR1 is shorter than the lighting color of IR2. In S1004, the user decides the exposure time and a camera gain for multi-spectral imaging. The UI management unit 514 may display a UI, which allows the user to select an exposure time and a camera gain common to the respective lighting colors, on the display unit 7 and receive the exposure time and camera gain common to the respective lighting colors. In addition, the UI management unit 514 may display a UI, which allows the user to select an exposure time and a camera gain for each lighting color, on the display unit 7 and receive the exposure time and the camera gain for each lighting color. In order to facilitate the adjustment of the exposure time and the camera gain, the UI management unit 514 may capture an image of the workpiece 2 with an exposure time and a camera gain which are temporarily set and display an imaging result (an image of the workpiece 2) on the display unit 7. In step S1005, the user selects a lighting color for photometric stereo. For example, the UI management unit 514 may display candidates of selectable lighting colors on the display unit 7 and receive selection of the lighting color performed by the user. For example, several light emitting elements can be selected from light emitting elements of the eight lighting colors from UV to IR2 and a white light emitting element. In S1006, the user decides an exposure time and a camera gain for photometric stereo. The UI management unit 514 may display a UI, which allows the user to select an exposure time and a camera gain, on the display unit 7 and receive the exposure time and the camera gain.

In S1007, the user executes inspection setting. Since the inspection unit 531 includes a plurality of inspection tools, the UI management unit 514 receives designation of parameters (an inspection region, a registered color, a tolerance, and the like) necessary for each inspection tool to execute inspection. The inspection region is set in the inspection tool. The registered color is set in the MSI processing unit 511. The tolerance is set in the determination unit 540. In addition, the UI management unit 514 also receives parameters relating to the movement correction to be described later.

Lighting Color Selection UI for Multi-Spectral Imaging

Figure 11:
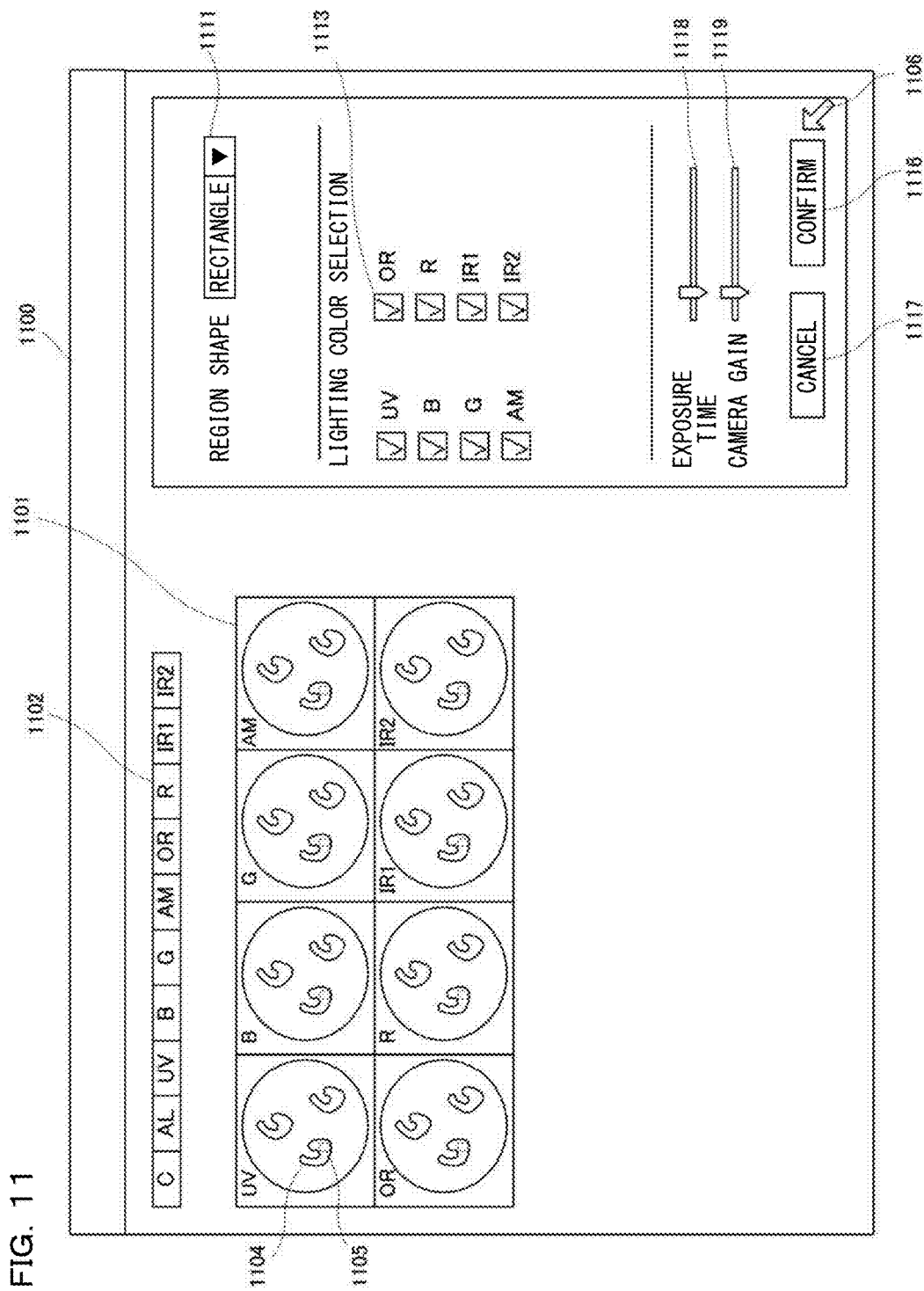
FIG. 11 is a view illustrating a user interface for selection of a wavelength.

FIG. 11 illustrates a user interface for selection of a wavelength (lighting color) for multi-spectral imaging. A lighting color selection UI 1100 is displayed on the display unit 7 by the UI management unit 514. An image selection button 1102 is a UI for selection of an image displayed in an image display region 1101, and sends a selection result to the image selection unit 515. In FIG. 11, C represents a color image created by combining a plurality of spectral images. AL represents all the spectral images of eight types. When AL is operated by a pointer 1106, the image selection unit 515 displays all the spectral images side by side in the image display region 1101. UV represents a spectral image acquired by an illumination beam of an ultraviolet wavelength. B represents a spectral image acquired by an illumination beam of a blue wavelength. G represents a spectral image acquired by an illumination beam of a green wavelength. AM represents a spectral image acquired by an illumination beam of an amber wavelength. OR represents a spectral image acquired by an illumination beam of an orange wavelength. R represents a spectral image acquired by an illumination beam of a red wavelength. IR1 and IR2 represent spectral images acquired by illumination beams of infrared wavelengths. Here, the wavelength of IR1 is shorter than the wavelength of IR2. In FIG. 11, the image of the workpiece 2 is displayed in the image display region 1101. In this example, a characteristic 1104 (for example, an ingredient such as a shrimp) of the workpiece 2 is also illustrated. When registering or inspecting a color of this characteristic 1104 as a registered color, the user operates a region shape selection menu 1111 in a pull-down format to select a shape of a designation region. Examples of the shape include a rectangle, a circle, an ellipse, an arbitrary shape, and the like. The region designation unit 516 arranges a frame line corresponding to the shape selected from the region shape selection menu 1111 in the image display region 1101.

In addition, the region designation unit 516 changes a position of a frame line 1105 or changes a size of the frame line 1105 when the frame line 1105 is dragged by the pointer 1106. A check box 1113 is a check box configured to select a lighting color used for multi-spectral imaging. The lighting color setting unit 517 recognizes a lighting color that is checked in the check box 1113 as the lighting color selected by the user. When a confirm button 1116 is operated, the lighting color setting unit 517, the lighting color setting unit 517 writes the checked lighting color in the setting information 523. When a cancel button 1117 is operated, the lighting color setting unit 517 cancels a state of the check box (a selected state of a lighting color) and returns to the immediately previous settings held in the setting information 523. A slide bar 1118 is a UI configured to manually adjust the exposure time. The exposure time can be increased or decreased by moving the slide bar 1118 right and left. A slide bar 1119 is a UI configured to manually adjust the camera gain. The camera gain can be increased or decreased by moving the slide bar 1119 right and left.

Here, the UI for selection of the lighting color and the UI for selection of the designation region are common, but may be different UIs.

Lighting Color Selection UI for Photometric Stereo

Figure 12:
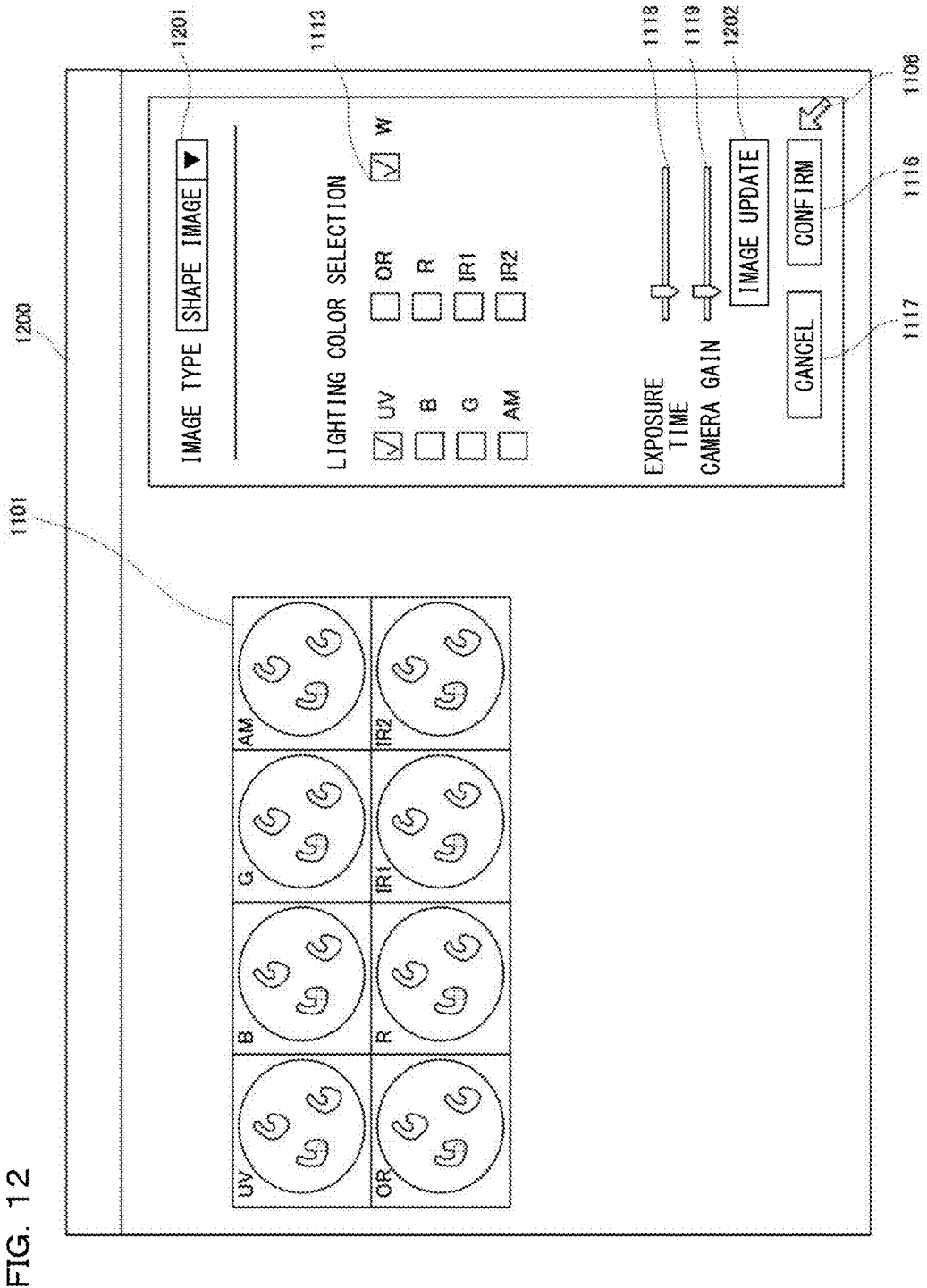
FIG. 12 is a view illustrating a user interface for selection of a wavelength.

FIG. 12 illustrates a user interface for selection of a lighting color for multi-spectral imaging. Elements which are common between FIGS. 12 and 11 are denoted by the same reference numerals in order to avoid repetition of the description. A lighting color selection UI 1200 is displayed on the display unit 7 by the UI management unit 514. One of differences of the lighting color selection UI 1200 from the lighting color selection UI 1100 is that an image type selection unit 1201 is provided. The image type selection unit 1201 is a pull-down menu that allows selection of an image relating to photometric stereo such as a shape image and a reflectance image. An image of a type selected by the image type selection unit 1201 is displayed in the image display region 1101. An image update button 1202 is a button to capture an image of the workpiece 2 again by the camera 4 according to parameters such as a lighting color, illumination intensity, an exposure time, and a camera gain, which are updated by the user, and to update the image displayed in the image display region 1101 to a new image. Although a plurality of images are displayed in this example, only an image obtained by being illuminated with an illumination beam of the lighting color selected by the check box 1113 may be displayed in the image display region 1101. The user can thus easily determine which illumination beam lighting color can accurately represent the irregularities of the surface of the workpiece 2 by displaying a plurality of images with different illumination beams. When a white LED is provided for each illumination block of the illumination device 3, the lighting color selection UI 1200 has a check box for selection of the white LED.

<Inspection Mode (Operation Mode)>

Figure 13:
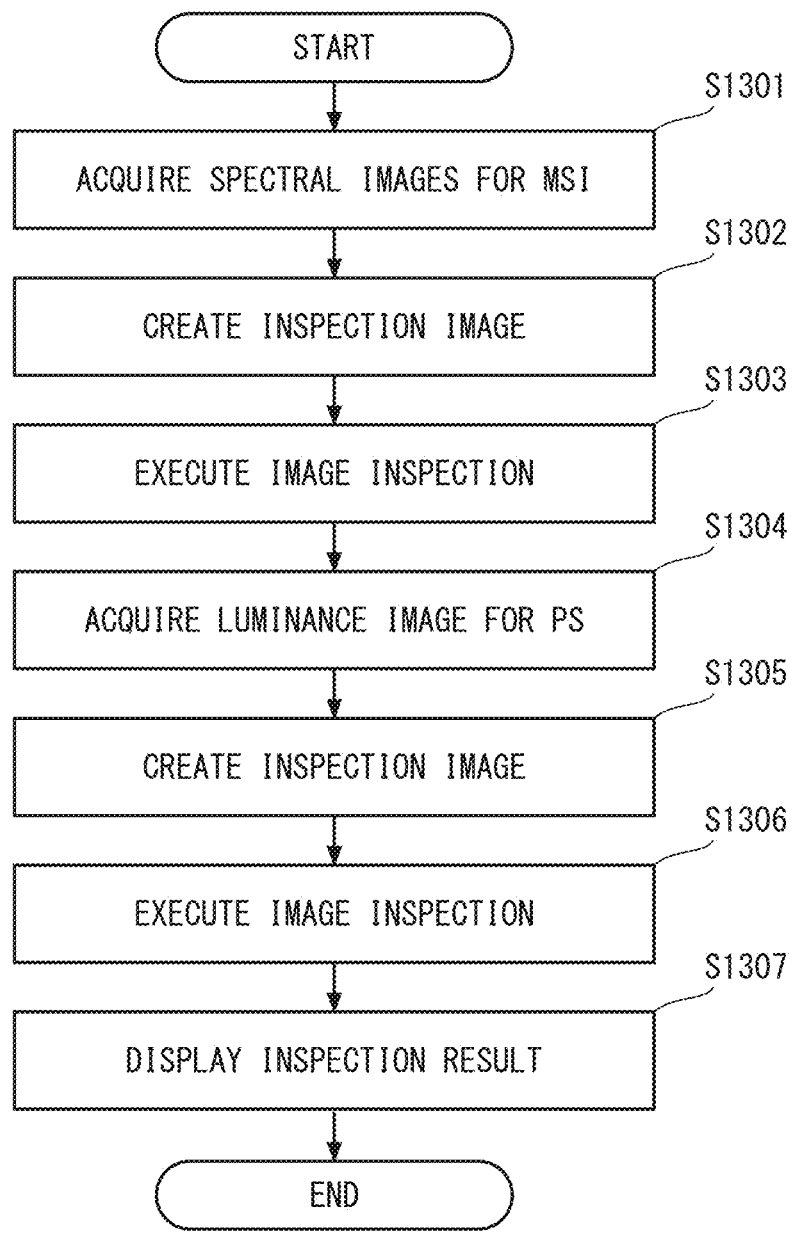
FIG. 13 is a flowchart illustrating an image inspection method.

FIG. 13 is a flowchart illustrating the inspection mode. Here, it is assumed that the image inspection by multi-spectral imaging and the image inspection by photometric stereo are executed for the same workpiece 2. Prior to describing FIG. 13, an example of the workpiece 2 and an example of the image inspection will be described.

Figure 14:
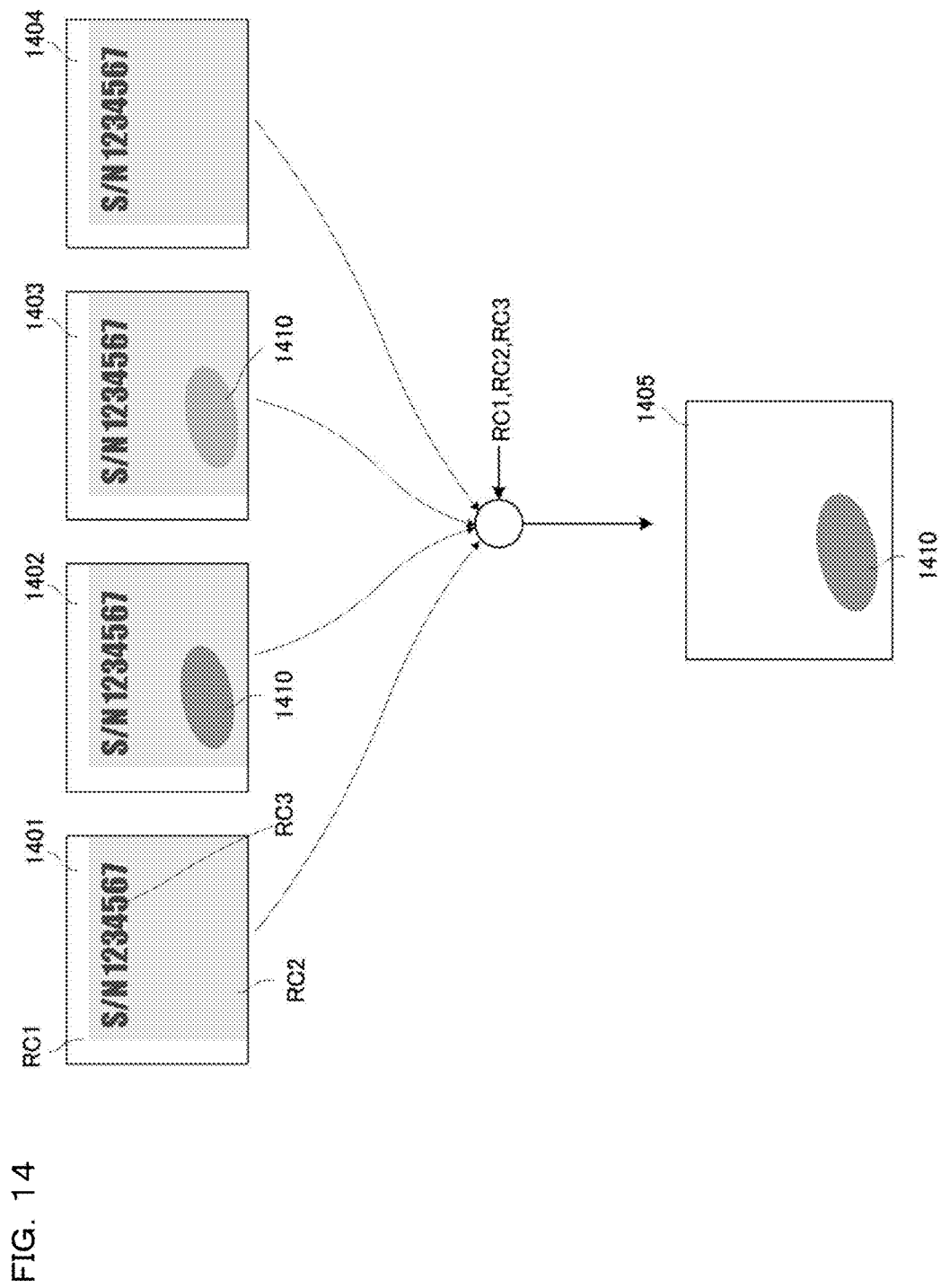
FIG. 14 is a view illustrating a procedure of creating a color inspection image.

FIG. 14 illustrates a concept of creating a color inspection image 1405 by multi-spectral imaging. The workpiece 2 in this example is a card. In addition, it is inspected whether the area of a "stain" formed on the card printed on a certain sheet exceeds a threshold. Here, it is assumed that four lighting colors are selected. A spectral image 1401 is a spectral image acquired with an illumination beam of a first lighting color W1. RC1 represents a color (first registered color) of the sheet. RC2 represents a color (second registered color) of the background of the card. RC3 represents a color (third registered color) of a character. These three colors form a set of registered colors and are held by the setting information 523. A spectral image 1402 is a spectral image acquired with an illumination beam of a second lighting color W2. A spectral image 1403 is a spectral image acquired with an illumination beam of a third lighting color W3. A spectral image 1404 is a spectral image acquired with an illumination beam of a fourth lighting color W1. A stain 1410 is not apparent in the spectral images 1401 and 1404, but is apparent in the spectral images 1402 and 1403. The spectral images 1401 to 1404 are subjected to color-gray conversion using the three registered colors, and the color inspection image 1405 is generated. In the color inspection image 1405, a color of the stain 1410 having the longest distance (Mahalanobis distance) is extracted based on the three registered colors. The area (blob) of the stain 1410 in the color inspection image 1405 is calculated, and whether the area exceeds the threshold is determined.

Figure 15:
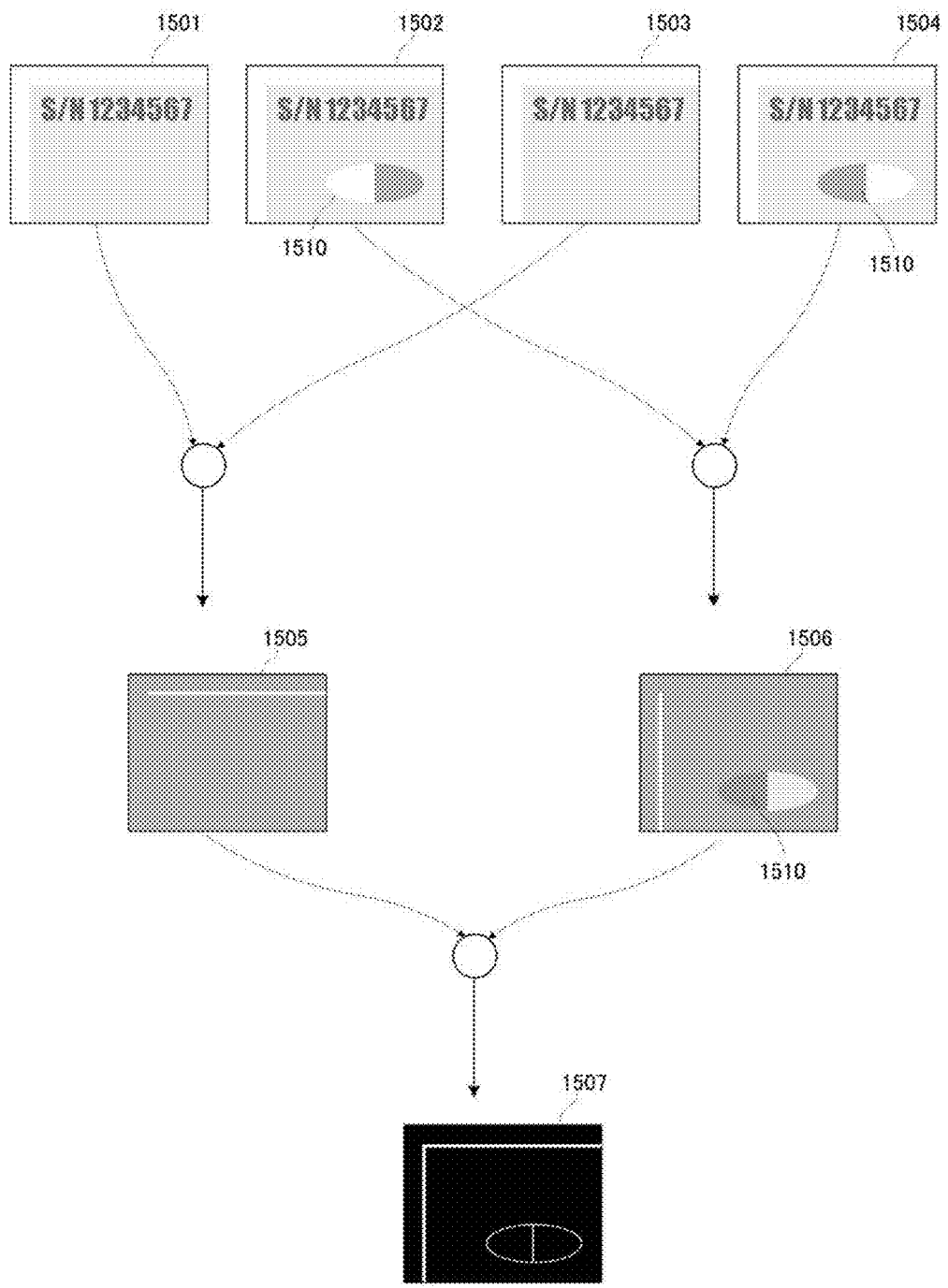
FIG. 15 is a view illustrating a procedure of creating a shape inspection image.

FIG. 15 illustrates a concept of creating a shape inspection image 1507 by photometric stereo. In this case, four luminance images 1501 to 1504 are generated by irradiation of illumination beams individually from four directions. The luminance image 1501 is an image acquired by irradiating the workpiece 2 with the illumination beam from a first direction. The luminance image 1502 is an image acquired by irradiating the workpiece 2 with the illumination beam from a second direction. The luminance image 1503 is an image acquired by irradiating the workpiece 2 with the illumination beam from a third direction. The luminance image 1504 is an image acquired by irradiating the workpiece 2 with the illumination beam from a fourth direction.

The first direction, the second direction, the third direction, and the fourth direction may correspond to the north, the east, the south, and the west, respectively. That is, the luminance image 1501 and the luminance image 1503 form a Y-direction pair, and the luminance image 1502 and the luminance image 1504 form an X-direction pair. A depression 1510 is formed in the workpiece 2. The depression 1510 becomes apparent or not depending on the direction of the illumination beam. An inclination image 1505 in the Y direction is created based on the luminance image 1501 and the luminance image 1503. An edge extending in the horizontal direction is extracted in the inclination image 1505. Similarly, an inclination image 1506 in the X direction is created based on the luminance image 1502 and the luminance image 1504. An edge extending in the vertical direction is detected in the inclination image 1506. Finally, a shape inspection image 1507 which is a contour extraction image is created based on the inclination image 1505 and the inclination image 1506. Presence or absence of a flaw such as the depression 1510 is inspected using the shape inspection image 1507. The shape inspection image 1507 is stored in the storage device 520 as the shape image data 525.

FIG. 13 will be described using the above example. In S1301, the processor 510 (the MSI processing unit 511) acquires the spectral images 1401 to 1404 for multi-spectral imaging according to the setting information 523. The MSI processing unit 511 sets a camera gain and an exposure time in the imaging control unit 513 according to the setting information 523. The imaging control unit 513 controls the camera 4 according to the set camera gain and exposure time and acquires the spectral images. In addition, the MSI processing unit 511 sets lighting colors (light emitting elements) to be turned on according to the setting information 523 and sets illumination intensity of each lighting color in the illumination control unit 512. The illumination control unit 512 turns on the light emitting element of the set lighting color with the set illumination intensity among the light emitting elements included in the light source group 501. As a result, the workpiece 2 is irradiated sequentially with illumination beams of the lighting colors set in advance by the user among UV to IR2, and a spectral image for each lighting color is generated. The acquired spectral image is stored in the storage device 520 as the spectral image data 521.

In S1302, the processor 510 (the MSI processing unit 511) creates the color inspection image 1405 (gray image) by performing the color-gray conversion on the acquired plurality of spectral images 1401 to 1404 using registered colors RC1 to RC3, and stores the created color inspection image 1405 in the storage device 520 as the gray image data 522.

In S1303, the processor 510 (the MSI processing unit 511) instructs the inspection unit 531 to perform image inspection. The inspection unit 531 measures the area of the stain 1410 in the color inspection image 1405, and sends a measurement result to the determination unit 540. The determination unit 540 determines as fail when the area of the stain 1410 exceeds the threshold, and determines as pass when the area of the stain 1410 is equal to or less than the threshold.

In S1304, the processor 510 (the PS processing unit 560) acquires the luminance images 1501 to 1504 for photometric stereo according to the setting information 523. The PS processing unit 560 sets a camera gain and an exposure time in the imaging control unit 513 according to the setting information 523. The imaging control unit 513 controls the camera 4 according to the set camera gain and exposure time and acquires the luminance images. In addition, the PS processing unit 560 sets lighting colors (light emitting elements) to be turned on according to the setting information 523 and sets illumination intensity of each lighting color in the illumination control unit 512. The illumination control unit 512 turns on the light emitting element of the set lighting color with the set illumination intensity among the light emitting elements included in the light source group 501. In the photometric stereo, a plurality of light emitting elements having different lighting colors may be simultaneously turned on. In addition, a white light emitting element that outputs a white illumination beam may be turned on. However, irradiation directions of the illumination beams are different for each luminance image. That is, the illumination control unit 512 turns on the light emitting element of the lighting color selected for irradiation of the illumination beam from the first direction. As a result, the imaging control unit 513 acquires the luminance image 1501. Next, the illumination control unit 512 turns on the light emitting element of the lighting color selected for irradiation of the illumination beam from the second direction. As a result, the imaging control unit 513 acquires the luminance image 1502. Next, the illumination control unit 512 turns on the light emitting element of the lighting color selected for irradiation of the illumination beam from the third direction. As a result, the imaging control unit 513 acquires the luminance image 1503. Finally, the illumination control unit 512 turns on the light emitting element of the lighting color selected for irradiation of the illumination beam from the fourth direction. As a result, the imaging control unit 513 acquires the luminance image 1504. The plurality of acquired luminance images are stored in the storage device 520 as the luminance image data 524.

In S1305, the processor 510 (the PS processing unit 560) creates the shape inspection image 1507 based on the plurality of acquired luminance images 1501 to 1504, and stores the created shape inspection image 1507 in the storage device 520 as the shape image data 525. As illustrated in FIG. 15, the PS processing unit 560 creates the inclination image 1505 in the Y direction and the inclination image 1506 in the X direction based on the luminance images 1501 to 1504, and creates the shape inspection image 1507 based on these inclination images.

In S1306, the processor 510 (the PS processing unit 560) instructs the inspection unit 531 to perform image inspection. The inspection unit 531 measures the area of the depression in the shape inspection image 1507, and sends a measurement result to the determination unit 540. The determination unit 540 determines that there is a flaw when the area of the depression exceeds the threshold, and determines that there is no flaw when the area of the depression is equal to or less than the threshold.

In S1307, the processor 510 (the UI management unit 514) displays a result of image inspection by multi-spectral imaging and a result of image inspection by photometric stereo on the display unit 7.

In this example, S1301 to S1303 which are processes relating to the multi-spectral imaging are executed first, and then, S1305 to S1306 which are processes relating to the photometric stereo are executed. However, the order of the processes may be reversed. Further, S1301 and S1304 may be executed first, and then S1302 and S1305 may be executed, and 1303 and S1306 may be finally executed. For example, the imaging control unit 513 may successively generate the shape inspection image 1507 and the color inspection image 1405 based on a trigger signal input from a programmable controller (PLC) or a console connected to the image inspection device 8. Trigger signals may be individually input for the shape inspection image 1507 and the color inspection image 1405. In addition, a trigger signal may be input for each spectral image or for each direction image.

<Moving Object Correction>

Figure 16:
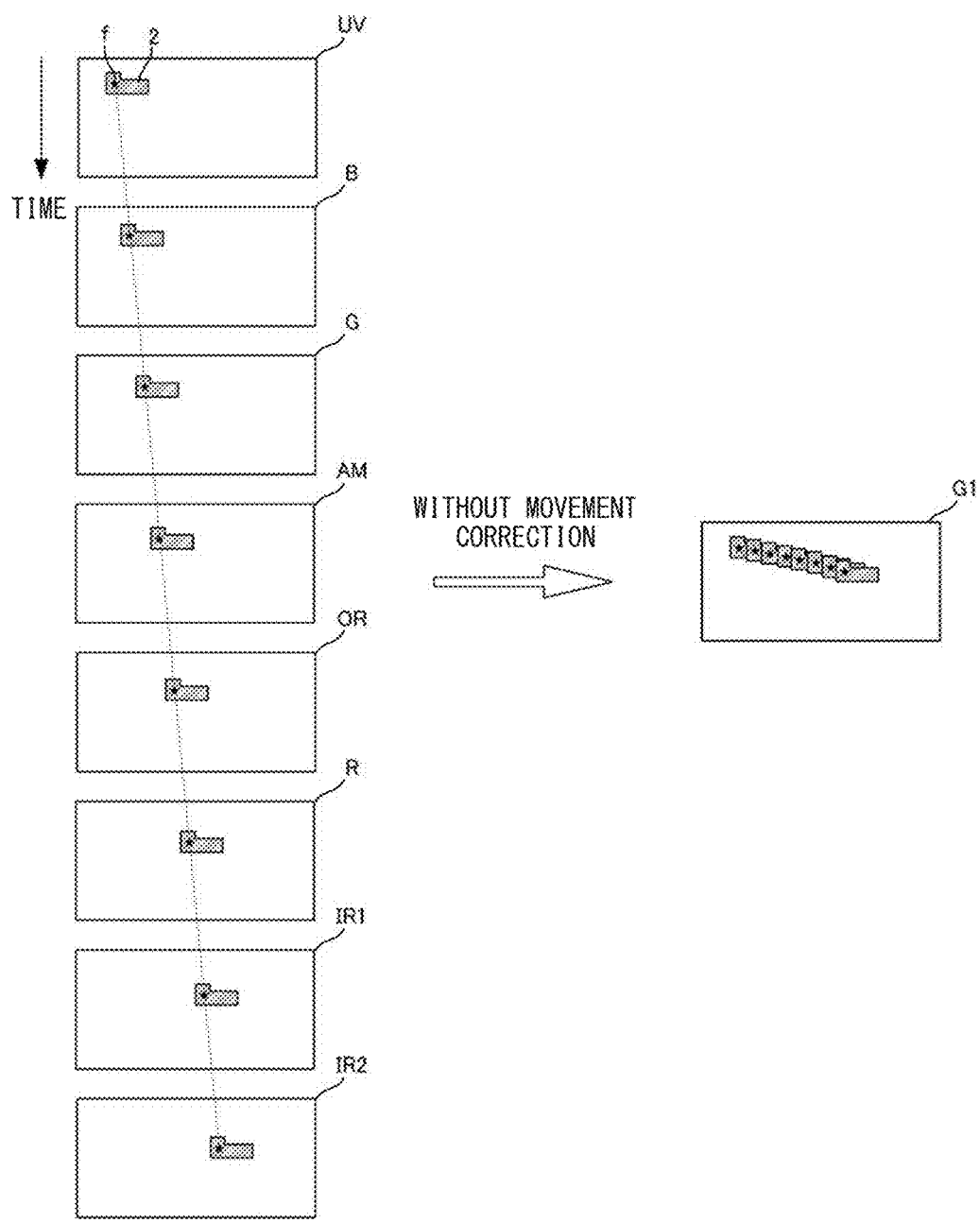
FIG. 16 is a view for describing a reason why movement correction is necessary.

In the multi-spectral imaging, the workpiece 2 is irradiated with illumination beams of a large number of lighting colors one by one, and a large number of spectral images are generated. For example, as illustrated in FIG. 16, the workpiece 2 is sequentially irradiated with illumination beams of eight types of lighting colors from UV to IR2 so that eight spectral images are obtained, and one gray image is further created based on the eight spectral images. When the workpiece 2 is conveyed on the line 1, a position of the workpiece 2 in the first UV image and a position of the workpiece 2 in the eighth IR2 image deviate from each other. A deviation amount of the position of the workpiece 2 increases as the number of lighting colors increases and as conveyance speed of the line 1 increases. It is difficult to obtain a correct gray image if a gray image G1 is created ignoring this deviation, and thus, the accuracy of image inspection deteriorates. Accordingly, if a gray image is created after performing movement correction on the workpiece 2, a correct gray image is created. The workpiece is illuminated from the different directions to generate a large number of luminance images in the photometric stereo. Accordingly, the movement correction is also necessary for the photometric stereo.

Figure 17:
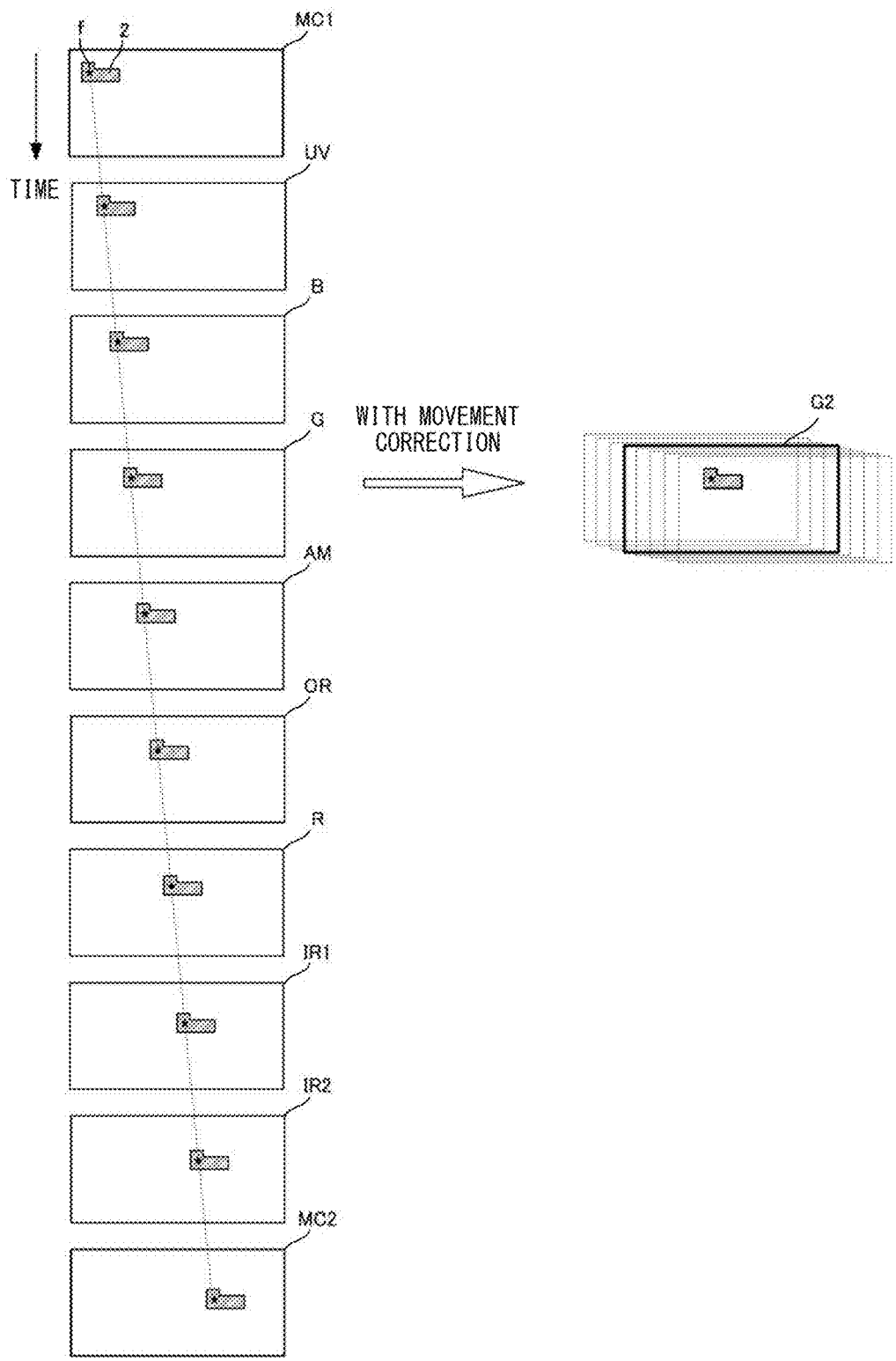
FIG. 17 is a view for describing a concept of movement correction.

FIG. 17 illustrates a concept of the movement correction. In this example, images MC1 and MC2 for the movement correction are acquired before and after the eight types of spectral images for multi-spectral imaging are acquired. Since conveying speed of the workpiece 2 on the line 1 is constant, positions of the workpiece 2 in the respective images draw a linear locus. Accordingly, if a correspondence relationship (a deviation amount in an x-direction and a deviation amount in a y-direction) of coordinates of pixels constituting the workpiece 2 in each spectral image is obtained, it is possible to create a gray image G2 by superimposing the positions of the workpiece 2 in the respective spectral images on each other. More specifically, a characteristic f of the workpiece 2 is detected by pattern search performed by the search unit 532 in the corrected images MC1 and MC2, and positions p1 and p2 of the characteristic f are obtained, respectively, from the images MC1 and MC2. The characteristic f may be a shape, an edge (an interval between two characteristic edges), or the like that can be detected by the pattern search. If a linear equation indicating changes of the positions p1 and p2 is obtained, it is possible to correct the position of the workpiece 2 in each spectral image. That is, the conversion formula of coordinates indicating the correspondence relationship in the coordinate system in each spectral image is decided.

When the workpiece 2 linearly moves, it is possible to perform the movement correction using two movement correction images. When the workpiece 2 moves non-linearly, three or more movement correction images are required. Here, a case where two movement correction images are used will be mainly described in order to simplify the description.

Figure 18:
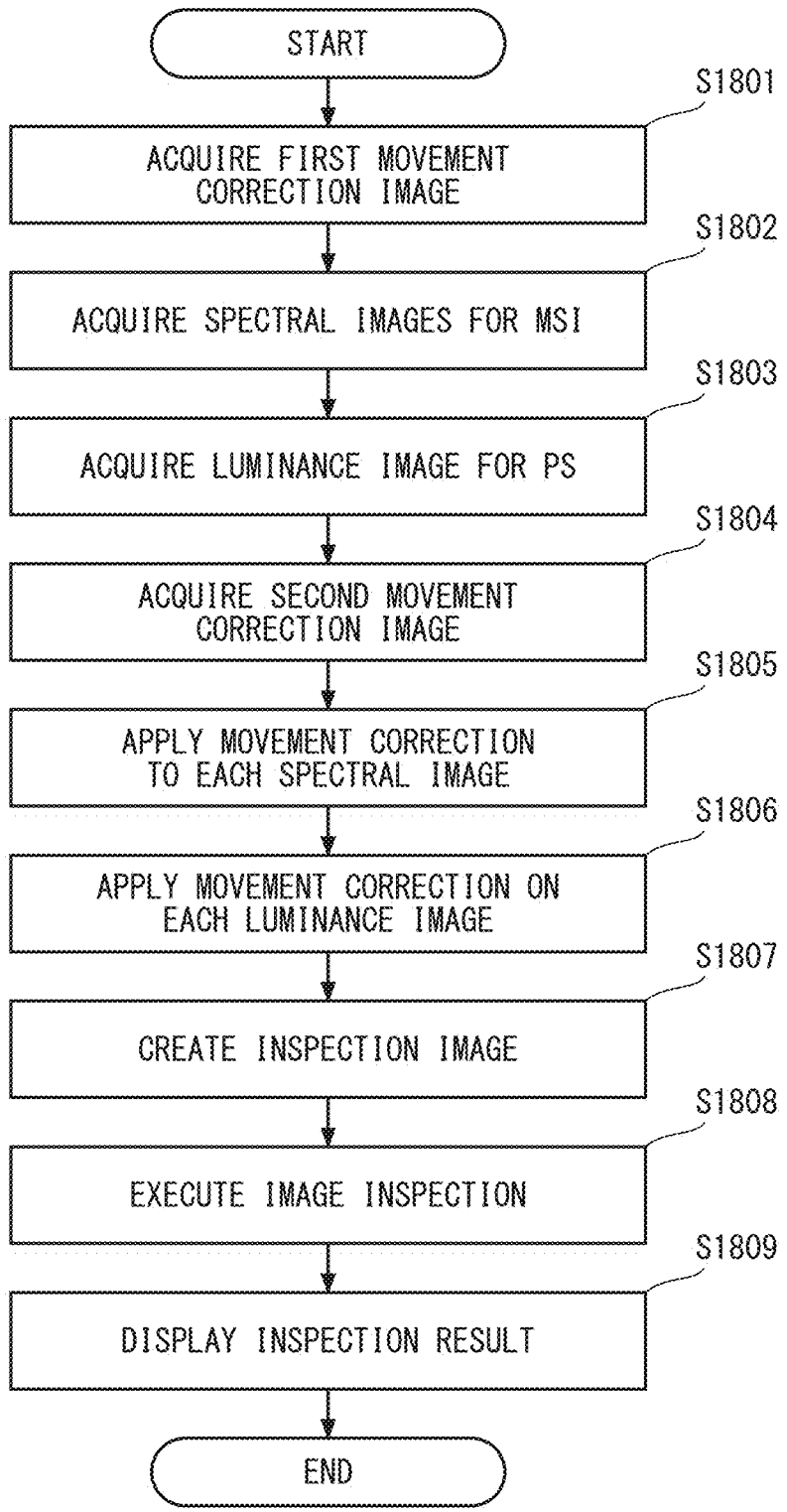
FIG. 18 is a flowchart illustrating an image inspection method including movement correction.

FIG. 18 is a flowchart illustrating image inspection including the movement correction. In S1801, the processor 510 acquires the first movement correction image MC1. The processor 510 decides lighting colors of illumination beams of the first movement correction image MC1 according to the setting information 523, and sets the decided lighting color in the illumination control unit 512. The illumination control unit 512 instructs the illumination control board 40 to turn on a light emitting element of the designated lighting color. The illumination control board 40 turns on the light emitting element of the designated lighting color. The processor 510 sets an imaging condition (an exposure condition and the like) according to the setting information 523 in the imaging control unit 513, and causes the imaging control unit 513 to acquire an image of the workpiece 2. The imaging control unit 513 controls the camera 4 according to the designated imaging condition to acquire the first movement correction image MC1 which is the image of the workpiece 2 and writes the first movement correction image MC1 in the storage device 520.

In S1802, the processor 510 (the MSI processing unit 511) acquires spectral images for multi-spectral imaging. S1802 is the same process as S1301. In S1803, the processor 510 (the PS processing unit 560) acquires spectral images for photometric stereo. S1803 is the same process as S1305.

In S1804, the processor 510 acquires a second movement correction image. The processor 510 decides lighting colors of illumination beams of the second movement correction image MC2 according to the setting information 523, and sets the decided lighting color in the illumination control unit 512. The illumination control unit 512 instructs the illumination control board 40 to turn on a light emitting element of the designated lighting color. The illumination control board 40 turns on the light emitting element of the designated lighting color. The processor 510 sets an imaging condition (an exposure condition and the like) according to the setting information 523 in the imaging control unit 513, and causes the imaging control unit 513 to acquire an image of the workpiece 2. The imaging control unit 513 controls the camera 4 according to the designated imaging condition to acquire the second movement correction image MC2 which is the image of the workpiece 2 and writes the first movement correction image MC1 in the storage device 520.

In S1805, the processor 510 causes the image processing unit 530 (the movement correction unit 533) to calculate a parameter for movement correction, and applies the movement correction to each spectral image using the parameter. The movement correction unit 533 causes the search unit 532 to search a characteristic in the first movement correction image MC1 and to search a characteristic in the second movement correction image MC2. The movement correction unit 533 calculates a change amount between a position of the characteristic in the first movement correction image MC1 and a position of the characteristic in the second movement correction image MC2. The movement correction unit 533 corrects a correspondence relationship between coordinates of the respective pixels in the plurality of spectral images based on the change amount. For example, a correspondence relationship between coordinates of the workpiece 2 in an UV image and coordinates of the workpiece 2 in an IR1 image is obtained. As illustrated in FIG. 17, the positions of the workpiece 2 in the respective spectral images are superimposed on each other by correcting the coordinates in the respective spectral images using the obtained correspondence relationship (coordinate conversion formula), whereby an accurate gray image is created.

In S1806, the processor 510 (the PS processing unit 560) applies the movement correction on the luminance image for photometric stereo. Since the correspondence relationship for movement correction has been acquired in S1805, the coordinates of the four luminance images for photometric stereo are corrected using this correspondence relationship. S1807 is a process that corresponds to S1302 and S1305, and a color inspection image is generated based on the movement-corrected spectral images, and a shape inspection image and an albedo image are generated based on the movement-corrected luminance images. S1808 corresponds to S1303 and S1306. S1809 corresponds to S1307.

Lighting Pattern

Figure 21:
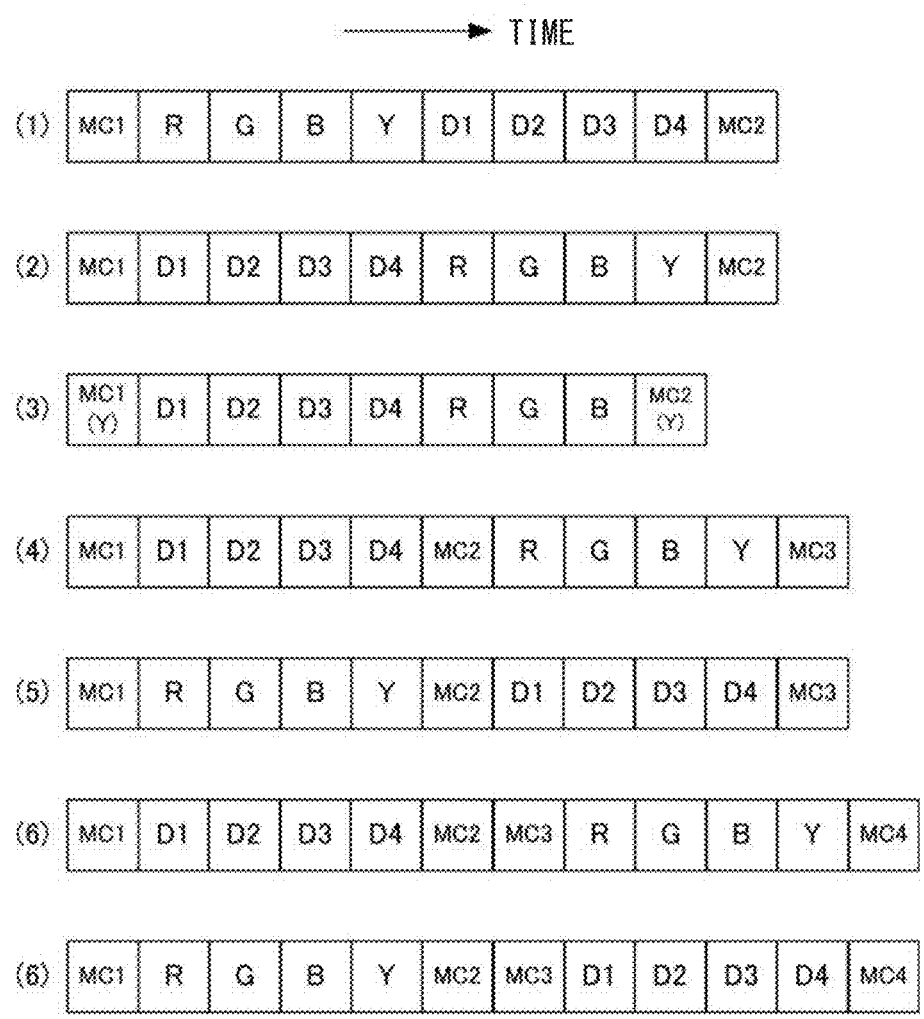
FIG. 21 is a view illustrating a lighting pattern of an illumination device.

According to FIG. 21, an example of a lighting pattern of light emitting elements configured to acquire spectral images and luminance images while performing movement correction is illustrated. Here, it is assumed that four lighting colors of R, G, B, and Y are used for multi-spectral imaging. Y is any lighting color other than RGB. MC1, MC2, MC2, and MC3 are common lighting colors for movement correction. D1, D2, D3, and D4 represent illumination directions of illumination beams of lighting colors for photometric stereo. R, G, B, Y, D1, D2, D3, D4, MC1, MC2, MC3, and MC4 may be understood as reference signs that represent images.

Cases (1) and (2) are lighting patterns for linear correction. Cases (1) and (2) illustrate that light emitting elements of lighting colors for movement correction are turned on before and after an image for multi-spectral imaging and an image for photometric stereo are acquired, and two movement correction images are acquired. In Case (1), the image for multi-spectral imaging is acquired earlier than the image for photometric stereo. In Case (2), the image for photometric stereo is acquired earlier than the image for multi-spectral imaging. In Cases (1) and (2), the two common movement correction images are used to perform movement correction on the image for multi-spectral imaging and the image for photometric stereo. It is necessary for acquisition intervals of the respective images to be equal intervals (constant time intervals) in order to execute the movement correction.

Case (3) is a case where spectral images for multi-spectral imaging are also used as movement correction images. As a result, the total number of images is reduced, and the imaging time is shortened. That is, it is possible to execute inspection on more images in a short time.

Cases (4) and (5) illustrate cases where three movement correction images are acquired. In Case (4), movement correction (linear correction) of an image for photometric stereo is executed using the movement correction image MC1 and the movement correction image MC2. In addition, movement correction (linear correction) of an image for multi-spectral imaging is executed using the movement correction image MC2 and the movement correction image MC3. In Case (5), movement correction of an image for multi-spectral imaging is executed using the movement correction image MC1 and the movement correction image MC2. In addition, movement correction of an image for photometric stereo is executed using the movement correction image MC2 and the movement correction image MC3. Non-linear correction such as quadratic function correction may be adopted instead of the linear correction.

Cases (6) and (7) illustrate cases where four movement correction images are acquired. In Case (6), movement correction (linear correction) of an image for photometric stereo is executed using the movement correction image MC1 and the movement correction image MC2. In addition, movement correction (linear correction) of an image for multi-spectral imaging is executed using the movement correction image MC3 and the movement correction image MC4. In Case (7), movement correction of an image for multi-spectral imaging is executed using the movement correction image MC1 and the movement correction image MC2. In addition, movement correction of an image for photometric stereo is executed using the movement correction image MC3 and the movement correction image MC4.

<Setting UI of Inspection Tool>

Figure 19:
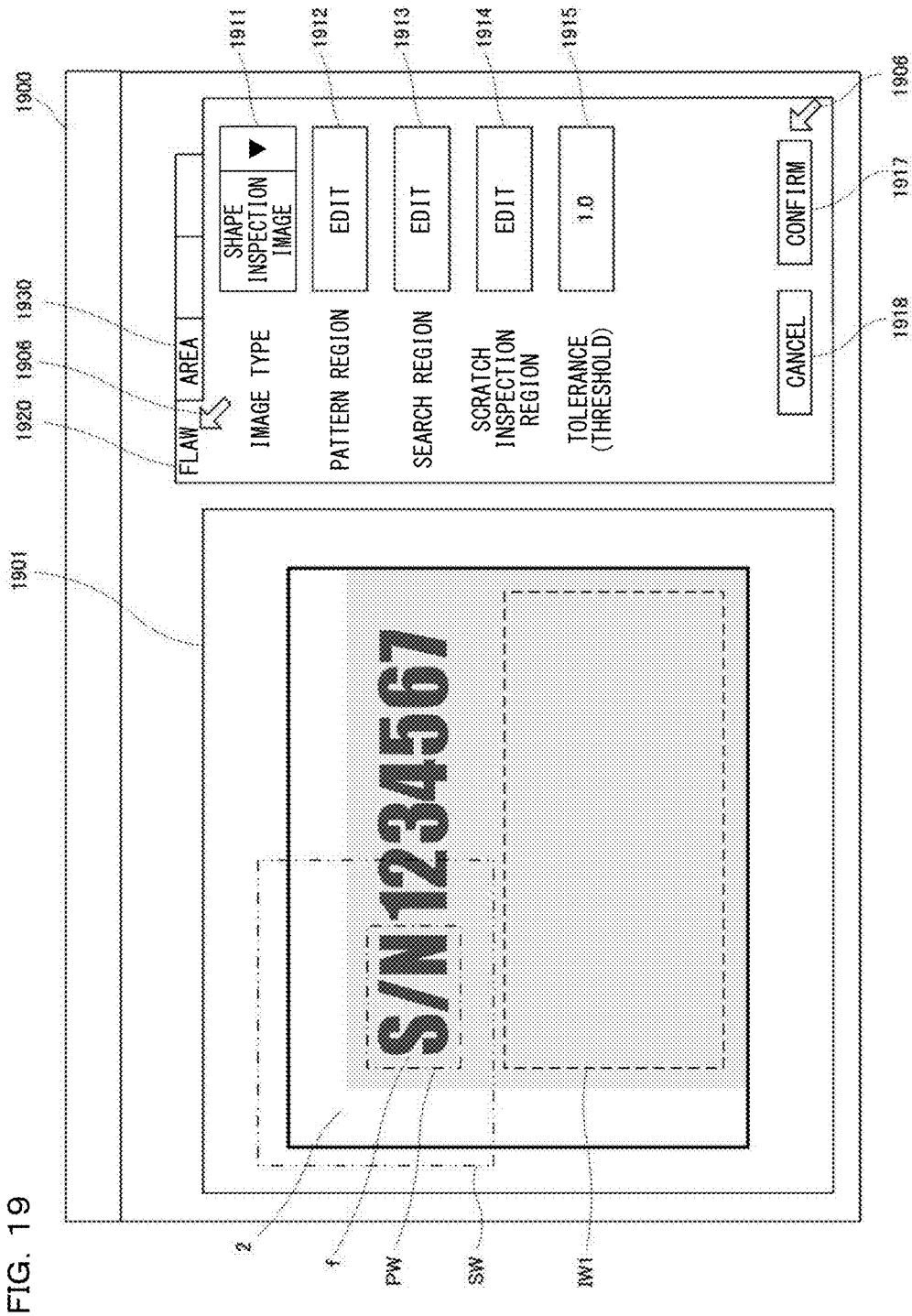
FIG. 19 is a view illustrating a user interface for setting of an inspection tool.

FIG. 19 illustrates a setting UI 1900 for setting of parameters of the inspection tool. Here, it is assumed that a plurality of inspection tools are set through the single setting UI 1900 for convenience of the description, but may be set through individual setting UIs, respectively. When a setting mode is selected by the user, the UI management unit 514 displays the setting UI 1900 on the display unit 7. A setting tab 1920 is a UI for setting of parameters relating to a flaw inspection tool. A setting tab 1930 is a UI for setting of parameters relating to an area inspection tool. In FIG. 19, the setting tab 1920 is selected by a pointer 1906. An image type setting unit 1911 is a pull-down menu for selection of an inspection image to which an inspection tool is applied. The shape inspection image, the albedo image, the color inspection image, and the like are registered in the pull-down menu. In FIG. 19, the shape inspection image generated by the photometric stereo is selected to inspect a flaw (depression or the like) of the workpiece 2. The image selection unit 515 of the UI management unit 514 reads the image selected by the image type setting unit 1911 from the storage device 520 and displays the read image in an image display region 1901. An edit button 1912 is a button configured to edit a size and a position of a pattern region PW which is a region including a characteristic f to be subjected to pattern search by the search unit 532. The characteristic f surrounded by the pattern region PW is stored in the storage device 520 as a registration pattern. An edit button 1913 is a button configured to edit a size and a position of a range (search region SW) for searching the characteristic f. The region designation unit 516 adjusts the sizes and positions of the pattern region PW and the search region SW according to the user's operation and saves an adjustment result in the setting information 523. A position and an angle of the workpiece 2 are not constant in images acquired by the camera 4. However, the characteristic f often falls within a certain region within each of the images. Thus, the search unit 532 obtains a position and an angle of a registration pattern by searching the registration pattern (characteristic f) within the search region SW. These position and angle are used to correct the position and angle of a flaw inspection region IW1 (position correction). An edit button 1914 is a button configured to edit a size and the position of the flaw inspection region IW1. The region designation unit 516 adjusts the size and the position of the flaw inspection region IW1 according to the user's operation and saves an adjustment result in the setting information 523. The inspection unit 531 calculates the area of the flaw in the flaw inspection region IW1. A tolerance input unit 1915 is a text box that receives an input of the tolerance (threshold) serving as a reference for determination on the presence or absence of the flaw by the determination unit 540. A confirm button 1917 is a button configured to confirm settings relating to the inspection tool. A cancel button 1918 is a button configured to cancel the current settings and return to immediately preceding settings or default settings.

Figure 20:
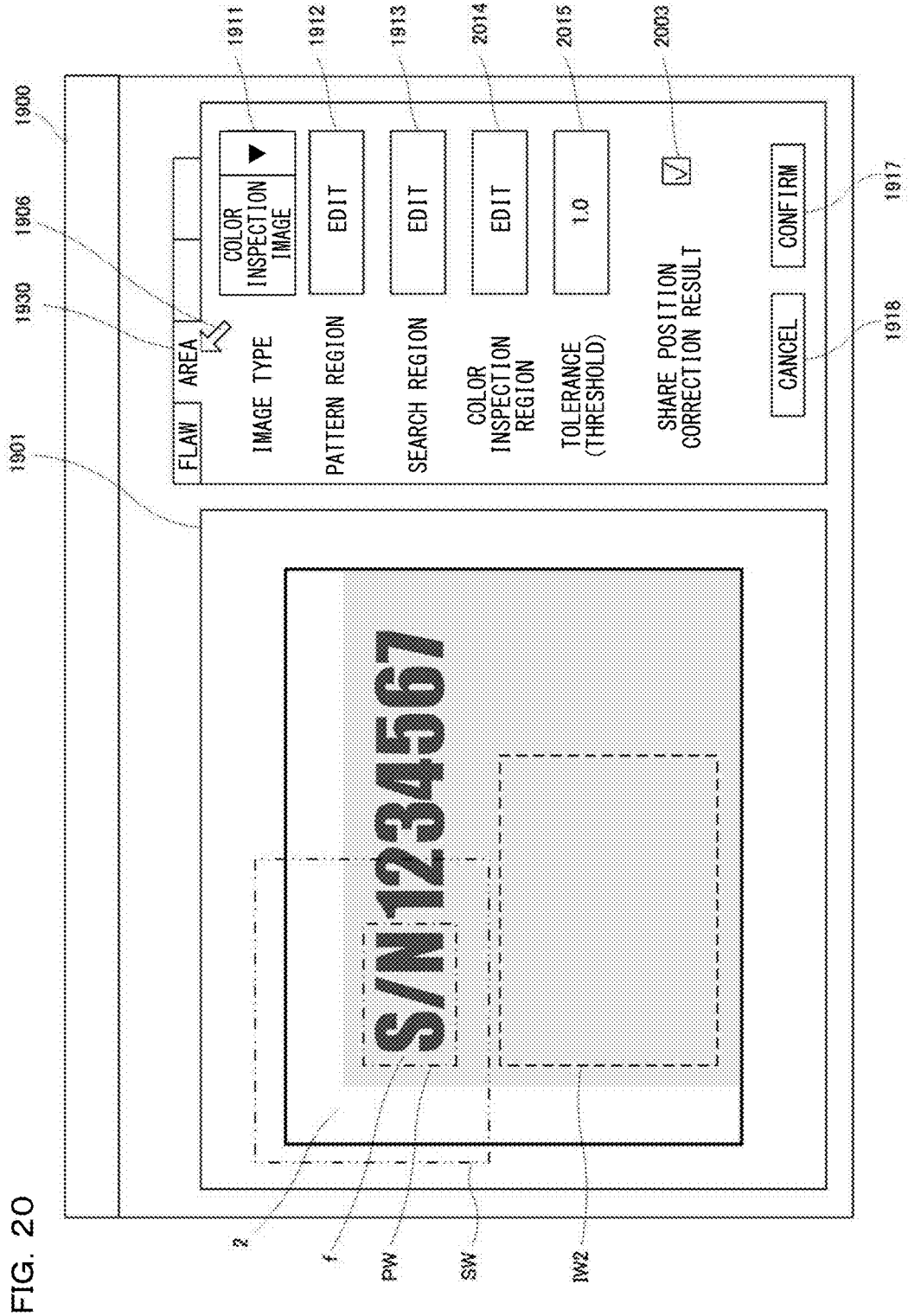
FIG. 20 is a view illustrating a user interface for setting of an inspection tool.

FIG. 20 illustrates the setting UI 1900 for setting of parameters of the inspection tool. Here, the settings relating to the area inspection tool and settings on a pattern search are received using the single UI for convenience of the description, but may be received by different UIs, respectively. In addition, the setting tab 1930 for setting of parameters relating to the area inspection tool is selected by the pointer 1906 in this example. Items common to the setting tab 1920 among the setting items of the setting tab 1930 are denoted by the same reference numerals. In this example, the color inspection image is selected by the image type setting unit 1911 in order to inspect presence or absence of a stain by the area inspection tool. An edit button 2014 is a button configured to edit a position and a size of a color inspection region IW2. When the edit button 2014 is clicked, the UI management unit 514 changes the position and size of the color inspection region IW2 according to the operation of the pointer 1906. The region designation unit 516 adjusts the size and the position of the color inspection region IW2 according to the user's operation and saves an adjustment result in the setting information 523. A tolerance input unit 2015 is a text box that receives an input of the tolerance (threshold) serving as a reference for determination on presence or absence of the stain. A check box 2003 is a check box configured to select whether to use a position correction result of an inspection region specified by another inspection tool for position correction of the color inspection region IW2 of an area measurement tool. When the check box 2003 is checked, the inspection unit 531 corrects the position and an angle of the color inspection region IW2 using the position information (position and angle) of the workpiece 2 specified in the flaw inspection tool. The check box 2003 may be provided in the setting tab 1920. In this case, the inspection unit 531 corrects the position and angle of the flaw inspection region IW1 using the position information (position and angle) of the workpiece 2 specified in the area inspection tool. In particular, when the workpiece 2 is inspected off-line and luminance images for photometric stereo and spectral images for multi-spectral imaging are successively acquired, there is almost no change in the position and angle of the workpiece 2 in the middle of acquiring these images. Therefore, it is possible to share the position correction result of the inspection region among a plurality of inspection tools, and the total inspection time is shortened.

SUMMARY

According to the present embodiment, the illumination device 3 is an example of an illumination unit which has three or more illumination blocks that irradiate a target object (for example, the workpiece 2) with illumination beams from different directions, respectively. Each illumination block is provided with a plurality of light emitting elements (for example, the LEDs 33) that generate illumination beams having different lighting colors, respectively. The camera 4 is an example of the imaging unit that receives the light reflected from the target object illuminated by the illumination beams and generates images of the target object. The processor 510 is an example of a control unit that controls the illumination unit to simultaneously turn on light emitting elements of the same lighting color included in the three or more illumination blocks, respectively, and to irradiate the target object sequentially with the illumination beams while changing lighting colors, and controls the imaging unit so as to generate a plurality of spectral images with different lighting colors of illumination beams. In addition, the processor 510 is an example of a control unit that controls the illumination unit to sequentially turn on the light emitting elements of the same lighting color included in each of the three or more illumination blocks and to irradiate the target object with the illumination beams, and controls the imaging unit so as to generate a plurality of direction images having mutually different irradiation directions of illumination beams. In this manner, the processor 510 executes not only the acquisition of spectral images according to multi-spectral imaging but also the acquisition of direction images and reflectance images for photometric stereo. It is unnecessary for the processor 510 to constantly execute the acquisition of the spectral image and the acquisition of the reflectance image. The processor 510 (the MSI processing unit 511 and the PS processing unit 560) is an example of an image generation unit that generates inspection images based on a plurality of spectral images or a plurality of direction images. The inspection unit 531 is an example of an inspection unit that inspects a target object using the inspection images formed by the image generation unit. As described with reference to FIGS. 3A to 3E and the like, the plurality of light emitting elements that output the illumination beams having the same lighting color are arranged at equal intervals in the illumination device 3. As a result, it is possible to irradiate the target object with illumination beams from a uniform direction regarding the spectral image. In addition, it is possible to irradiate the target object with illumination beams having a uniform light amount in each direction regarding the direction image. In this manner, the camera 4 and the illumination device 3 can be shared between the multi-spectral imaging and the photometric stereo, and thus, it is possible to reduce the number of cameras and illumination devices to be installed according to the present embodiment. In addition, user's work such as adjustment of a distance between the imaging unit and the target object and focus adjustment of the imaging unit is also reduced. That is, the burden on the user is alleviated and the usability is improved.

The MSI processing unit 511 is an example of the image generation unit that generates a color inspection image in which each pixel has a value corresponding to a color of the target object based on the plurality of lighting color images. The inspection unit 531 is an example of the inspection unit that executes color inspection of the target object using the color inspection image generated by the image generation unit.

The PS processing unit 560 is an example of the image generation unit that generates a shape inspection image having a value corresponding to irregularities of the target object based on the plurality of direction images. The inspection unit 531 is an example of the inspection unit that executes shape inspection of the target object using the shape inspection image generated by the image generation unit.

The processor 510 may turn on all light emitting elements included in an illumination block to be turned on when generating the direction image. In general, white light is used as the illumination beam for photometric stereo. In the illumination device of the present embodiment, the plurality of light emitting elements having different lighting colors are provided in one block. Accordingly, it is possible to realize pseudo white light by simultaneously turning on the plurality of light emitting elements provided in one block constituting a certain illumination direction. That is, it is possible to omit a white light source.

Although the illumination device 3 has been described as having four illumination blocks in the present embodiment, it is sufficient as long as three or more illumination blocks are present. In addition, each of these illumination blocks may have a white light emitting element (a white LED or the like). In this case, the processor 510 may turn on the white light emitting element included in the illumination block to be turned on when generating the direction image. Accordingly, it becomes unnecessary to simultaneously turn on the plurality of light emitting elements having different lighting colors, and it may be possible to reduce power consumption relating to the illumination beam.

When generating the direction image, the processor 510 turns on a light emitting element that is included in the illumination block to be turned on and that generates illumination beam of a specific lighting color. When generating the shape inspection image or the albedo image by photometric stereo, appropriate lighting colors may be different depending on a surface property of the workpiece 2. Therefore, accurate shape inspection image and albedo image may be easily obtained by irradiating the workpiece 2 with the illumination beam of the specific lighting color.

As illustrated in FIGS. 11 and 12A, lighting color reception unit (the check box 1113) that receives selection of a specific lighting color performed by the user may be provided. As a result, the user can designate the lighting color of the illumination beam.

The processor 510 and the image processing unit 530 may analyze the shape inspection image acquired in the setting mode in which the shape inspection such as the inspection on the presence or absence of the depression is set. Further, the processor 510 or the image processing unit 530 may function as a lighting color selection unit that selects a specific lighting color to be turned on in the operation mode in which the shape inspection is executed based on such an analysis result. For example, the processor 510 or the image processing unit 530 may select a lighting color from which the highest contrast has been obtained among UV to IR2.

As described with reference to FIGS. 19 and 20, the display unit 7 functions as a display unit that displays the shape inspection image and the color inspection image in a switching manner in the setting mode in which parameters required for the shape inspection are set.

The display unit 7 may display the shape inspection image and the color inspection image at the same time. The user may be able to appropriately set the parameters necessary for the shape inspection by comparing the shape inspection image with the color inspection image.

As described with reference to FIGS. 19 and 20, the UI management unit 514 selects the image type to which each inspection tool is applied according to the instruction of the user. That is, the UI management unit 514 functions as a setting unit that sets different inspection tools for the shape inspection image and the color inspection image.

The inspection unit 531 includes various inspection tools. For example, the inspection tool set for the shape inspection image may include an inspection tool configured to inspect at least a flaw (irregularities or the like). The flaw such as depression appears clearly in the shape inspection image in some cases. Accordingly, the shape inspection image is suitable for the flaw inspection. In addition, the inspection tool set for the color inspection image may include an inspection tool configured to inspect at least an area (a blob such as a stain or the area). Since the stain and the like appear as changes in color, the color inspection image is suitable for the inspection on the stain and the like.

As described with reference to FIG. 20, the position information of the workpiece 2 may be shared among the plurality of inspection tools. That is, the image processing unit 530 (the inspection unit 531 or the search unit 532) may function as a correction unit that uses position information of the target object in one inspection tool between the inspection tool set for the shape inspection image and the inspection tool set for the color inspection image to correct a position of an inspection region of the other inspection tool between the inspection tool set for the shape inspection image and the inspection tool set for the color inspection image. Accordingly, it is possible to correct the position of the inspection region of each inspection tool with less information. In addition, by using an image in which the position of the characteristic pattern can be easily detected, the position detection accuracy is improved and the movement correction accuracy is also improved. It is a matter of course that the position of the workpieces 2 may be individually searched for each of the color inspection image and the shape inspection image, and the positions of the inspection regions may be individually corrected according to search results.

The processor 510 may control the illumination unit, the imaging unit, and the image generation unit based on the same trigger signal to successively generate the shape inspection image and the color inspection image. The trigger signal indicating an imaging timing may be input from the PLC or the console connected to the image inspection device as described above. In this case, the required number of spectral images and luminance images may be acquired by being triggered by one trigger signal. As a result, it is unnecessary for the user to instruct execution of imaging individually for the shape inspection image and the color inspection image, and the burden on the user may be alleviated.

As described with reference to FIGS. 3A to 3E, a diffusion plate may be installed between the illumination unit and the target object. For example, a bottom surface of the illumination device 3 may function as the diffusion plate.

The PS processing unit 560 may function as the image generation unit that creates an albedo image in which a reflectance of a surface of the target object is a pixel value based on the plurality of direction images. The inspection unit 531 may execute image inspection of the target object using the albedo image generated by the image generation unit.

As described with reference to FIGS. 3A to 3E, the plurality of light emitting elements that generate illumination beams having different lighting colors, respectively, are arranged at equal intervals in each illumination block. In addition, the number of the plurality of light emitting elements included in each illumination block may be n times (n is an integer of one or more) of the number of types of lighting colors of the plurality of light emitting elements. For example, when there are 16 types of lighting colors, 16 light emitting elements, 32 light emitting elements, 64 light emitting elements, and so on are provided in one illumination block. In this case, the number of light emitting elements of a certain type of lighting color in one illumination block is n.

What is claimed is:
1. An image inspection device comprising:
an illumination unit which includes three or more illumination blocks that irradiate a target object with illumination beams from mutually different directions, each of the illumination blocks including a plurality of light emitting elements that generate the illumination beams having mutually different lighting colors;
an imaging unit which receives light reflected from the target object illuminated by the illumination beams and generates an image of the target object;
a control unit which controls the illumination unit to simultaneously turn on light emitting elements of an identical lighting color included in each of the three or more illumination blocks and to irradiate the target object sequentially with illumination beams while changing lighting colors and controls the imaging unit so as to generate a plurality of spectral images having mutually different lighting colors of the illumination beams, and controls the illumination unit to sequentially turn on light emitting elements of an identical lighting color included in each of the three or more illumination blocks and to irradiate the target object with illumination beams, and controls the imaging unit so as to generate a plurality of direction images having mutually different irradiation directions of illumination beams;

an image generation unit which generates a color inspection image in which each pixel has a value corresponding to a color of the target object based on the plurality of spectral images and a shape inspection image using the principle of photometric stereo based on the plurality of direction images; and an inspection unit which inspects the target object using the color inspection image and the shape image formed by the image generation unit, wherein a plurality of light emitting elements that output illumination beams of an identical lighting color are arranged at equal intervals in the illumination unit.

2. The image inspection device according to claim 1, wherein the inspection unit executes color inspection of the target object using the color inspection image generated by the image generation unit.

3. The image inspection device according to claim 2, wherein the image generation unit generates the shape inspection image having a value corresponding to irregularities of the target object based on the plurality of direction images, and the inspection unit executes shape inspection of the target object using the shape inspection image generated by the image generation unit.

4. The image inspection device according to claim 3, wherein the control unit turns on a light emitting element that is included in an illumination block to be turned on and that generates an illumination beam of a specific lighting color when generating each of the plurality of direction images.

5. The image inspection device according to claim 4, further comprising a lighting color reception unit that receives selection of the specific lighting color performed by a user.

6. The image inspection device according to claim 4, further comprising a lighting color selection unit which selects the specific lighting color to be turned on in an operation mode in which the shape inspection is executed, by analyzing the shape inspection image acquired in a setting mode in which the shape inspection is set.

7. The image inspection device according to claim 3, further comprising:

a display unit which displays the shape inspection image and the color inspection image simultaneously or in a switching manner in a setting mode in which the shape inspection is set; and a setting unit which sets different inspection tools for the shape inspection image and the color inspection image, respectively.

8. The image inspection device according to claim 7, wherein the inspection unit for the shape inspection image includes an inspection tool configured to inspect at least a flaw.

9. The image inspection device according to claim 3, wherein the inspection unit for the color inspection image includes an inspection tool configured to inspect at least an area.

10. The image inspection device according to claim 9, further comprising a correction unit which uses position information of the target object in one inspection tool between the inspection unit for the shape inspection image and the inspection tool set for the color inspection image to correct a position of an inspection region of the other inspection tool between the inspection tool set for the shape inspection image and the inspection tool set for the color inspection image.

11. The image inspection device according to claim 3, wherein the control unit controls the illumination unit, the imaging unit, and the image generation unit based on an identical trigger signal to successively generate the shape inspection image and the color inspection image.

12. The image inspection device according to claim 1, wherein the control unit turns on all light emitting elements included in an illumination block to be turned on when generating each of the plurality of direction images.

13. The image inspection device according to claim 1, wherein each of the three or more illumination blocks has a white light emitting element, and the control unit turns on the white light emitting element included in an illumination block to be turned on when generating each of the plurality of direction images.

14. The image inspection device according to claim 1, further comprising a diffusion plate installed between the illumination unit and the target object.

15. The image inspection device according to claim 1, wherein the image generation unit is configured to create an albedo image in which a reflectance of a surface of the target object is a pixel value based on the plurality of direction images, and the inspection unit executes image inspection of the target object using the albedo image generated by the image generation unit.

16. The image inspection device according to claim 1, wherein a plurality of light emitting elements that generate illumination beams having mutually different lighting colors are arranged at equal intervals in each of the illumination blocks.

17. The image inspection device according to claim 1, wherein a number of the plurality of light emitting elements included in each of the illumination blocks is n times (n is an integer of one or more) of a number of types of lighting colors of the plurality of light emitting elements.

18. The image inspection device according to claim 1, wherein the control unit controls the illumination unit to irradiate the target object with illumination beams of an identical color having different irradiation directions by sequentially turning on the light emitting elements of the identical lighting color included in each of the three or more illumination blocks, and controls the imaging unit to generate a plurality of direction images having the mutually different irradiation directions, the image generation unit generates the shape inspection image having a value corresponding to irregularities of the target object based on the plurality of direction images, the inspection unit executes shape inspection of the target object using the shape inspection image generated by the image generation unit, the control unit controls the illumination unit to simultaneously turn on the light emitting elements of the identical lighting color included in each of the three or more illumination blocks and to irradiate the target object sequentially with illumination beams while changing lighting colors, and controls the imaging unit to generate a plurality of spectral images having mutually different lighting colors of the illumination beams, the image generation unit combines the plurality of spectral images to generate the color inspection image in which each pixel has a value corresponding to a color of the target object, and the inspection unit executes color inspection of the target object using the color inspection image generated by the image generation unit.

* * * * *